United States Patent

[19]

Matsumoto et al.

[11] Patent Number: 6,057,324

[45] Date of Patent: May 2, 2000

[54] SUBSTITUTED AMIDINOBENZENE DERIVATIVES AND MEDICINAL COMPOSITIONS THEREOF

[75] Inventors: Yuzo Matsumoto, Toride; Seijiro Akamatsu, Tsukuba; Masato Ichihara, Tsukuba; Tomihisa Kawasaki, Tsukuba; Seiji Kaku, Tsukuba; Isao Yanagisawa, Tokyo, all of Japan

[73] Assignees: Yamanouchi Pharmaceutical Co., Ltd, Tokyo, Japan; Merck Patent Gesellschaft Mit Beschrankter Haftung, Darmstadt, Germany

[21] Appl. No.: 09/194,202

[22] PCT Filed: May 28, 1997

[86] PCT No.: PCT/JP97/01804

§ 371 Date: Nov. 20, 1998

§ 102(e) Date: Nov. 20, 1998

[87] PCT Pub. No.: WO97/45413

PCT Pub. Date: Apr. 12, 1997

[30] Foreign Application Priority Data

May 30, 1996 [JP] Japan .................................. 8-137273

[51] Int. Cl.$^7$ ........................ C07D 401/00; A61K 31/495
[52] U.S. Cl. ........................................... 514/255; 544/360
[58] Field of Search ................................. 544/238, 319, 544/360; 514/269, 252, 255

[56] References Cited

FOREIGN PATENT DOCUMENTS 542363  2/1995  European Pat. Off. .

OTHER PUBLICATIONS

Eldred, C.D. et al., "Orally Active Non–Peptide Fibrinogen Receptor (GpIIb/IIIa) Antagonist: Identification of 4–(4–(4–(Aminominomethyl)phenyl)–1–piperazinyl)–1–piperidineacetic Acid as a Long–Acting, Broad–Spectrum Antithrombotic Agent", 1994, J. Med. Chem., vol. 37, No. 23, pp. 3882–3885.

Stilz H.U. et al., "Discovery of an Orally Active Non–peptide Fibrinogen Receptor Antagonist", May 24, 1996, J. Med. Chem., vol. 39, No. 11, pp. 2118–2122.

*Primary Examiner*—Richard L. Raymond
*Assistant Examiner*—Sudhaker B. Patel
*Attorney, Agent, or Firm*—Finnegan, Henderson, Farabow, Garrett & Dunner, L.L.P.

[57] ABSTRACT

A substituted-amidinobenzene derivative of the following general formula (I) or a salt thereof, and a pharmaceutical composition comprising said derivative or a salt thereof and a pharmaceutically acceptable carrier.

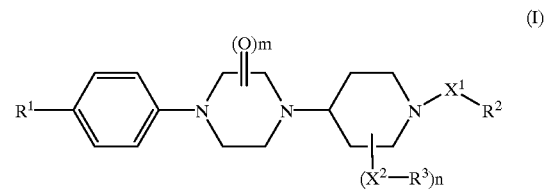

(I)

(the symbols in the above formula have the following meanings:

$R^1$: a group which can be converted into an amidino group in vivo;

$R^2$ and $R^3$: the same or different and each represents a carboxyl group or a group which can be converted into a carboxyl group in vivo;

$X^1$ and $X^2$: the same or different and each represents a lower alkylene group;

m: 0, 1 or 2;

n: 0 or 1, provided that n=1 when m=0.

They have GPIIb/IIIa receptor antagonizing activity and are useful as medicines for ameliorating ischemic cardiac disorders, adminicula in cardiosurgery operations or in vascular surgery operations, medicines for ameliorating cerebrovascular disorders, And medicines for ameliorating peripheral artery disorders. In addition, they are useful as a prodrug excellent in peroral absorbability and sustainment of the effect.

10 Claims, 1 Drawing Sheet

SUBSTITUTED AMIDINOBENZENE DERIVATIVES AND MEDICINAL COMPOSITIONS THEREOF

TECHNICAL FIELD

The present invention relates to novel substituted-amidinobenzene derivatives and their salts which are useful as medicines, especially as GPIIb/IIIa antagonists.

BACKGROUND ART

For a long period of time after the finding by Donne in 1842 (see *C.R. Acad. Sci.* (Paris), 14, 336–368, 1842); blood platelets have been considered as the component in blood which is necessary for hemostasis. At present, it has been clarified that blood platelets not only play the principal part in the hemostatic mechanism of blood but also are multi-functional as participating in the creation of arteriosclerosis, cardiovascular system disorders including thrombotic disorders, cancer metastases, inflammations, rejections after transplants, and also immunoreactions, etc., which are clinically important. The thrombotic disorders and ischemic disorders are therapeutically treated by restoring the circulation of the blood by the application of medicines or by physical means. However, a clinically problematic phenomena has been found recently that, after the restoration of the blood circulation, the activation, the adhesion and the aggregation of blood platelets are promoted based on the damage of the blood vessel tissue including endothelial cells and the unbalanced systemic fibrinolysis-coagulation equilibrium caused by the medicines itself, and the like. For instance, it has been clarified that, after the circulation of the blood has been restored by thrombolytic therapy using t-PA (tissue Plasminogen Actitor) or the like, the fibrinolytic activity and the coagulating activity are activated to break the systemic fibrinolysis-coagulation equilibrium. Clinically, it causes re-occlusion and is therefore seriously problematic in the therapy (see *J. Am. Coll. Cardiol.*, 12, 616–623, 1988). On the other hand, a PTCA Percutaneous transluminal coronary angioplasty) therapy has been rapidly popularized, with producing good results in some degree, for curing disorders as based on coronary stenosis and aortostenosis, such as stenocardia, myocardial infarction, etc. However, this therapy involves serious problems in that it damages the blood vessel tissue including endothelial cells to cause acute coronary obstruction and even re-stenosis which occurs in about 30% of therapeutical cases. Blood platelets play the principal role in various thrombotic disorders (e.g., re-occlusion) following such blood circulation-restoring therapy. Therefore, the effectiveness of anti-platelet agents would be expected for such disorders. However, conventional anti-platelet agents have not as yet been verified to be satisfactorily effective. GPIIb/IIIa is a platelet membrane glycoprotein which is one of the integrin family (see *Blood*, 80, 1386–1404, 1992). This integrin binds to adhesive proteins such as fibrinogen, von Willebrand factor, etc., and have an important function at the terminal in blood platelet aggregation. Monoclonal antibodies against GPIIb/IIIa, peptides having an RGD sequence and the like have potent platelet aggregation inhibiting activity, and some of which have already been put into clinical examinations.

Non-peptidic, low molecular weight GPIIb/IIIa antagonists are known in a published Japanese patent application (kokai) 4-288051 (sulfonamide fibrinogen receptor antagonists of the following representative compound,

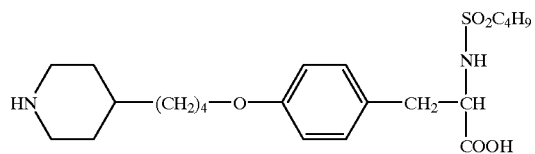

and a published Japanese patent application (kokai) 6-25227 (cyclic imino derivatives of the following representative compound,

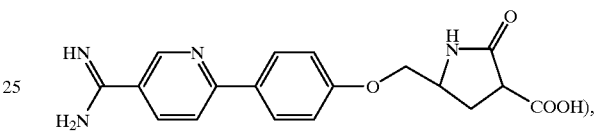

and are disclosed by Leo et al. (see *Journal of Medicinal Chemistry*, 35, 4393–4407, 1992) in which the following representative compound is disclosed.

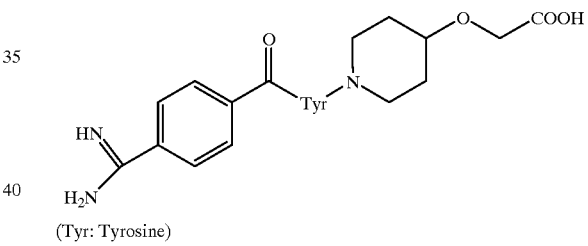

(Tyr: Tyrosine)

The piperizine acetic acid derivatives of the following general formula are disclosed in a published PCT patent application WO093/10091.

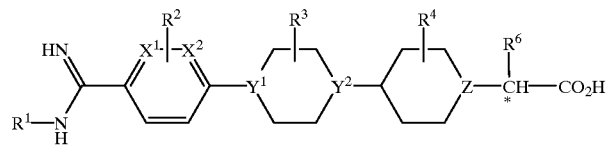

(in which $X^1$ and $y^1$, which may be the same or different, represent CH or N;

$X^2$ represents CH or, when $X^1$ represents CH, may also represent N;

$y^2$ represents N or, when $y^1$ represents N, may also represent CH;

z represents N or $N^+R^5$;

$R^1$ represents a hydrogen atom or a hydroxyl, $C_{1-4}$ alkyl or 2,2,2-trifluoroethyl group;

$R^2$ represents a hydrogen atom or, when both $X^1$ and $X^2$ represent CH, may also represent a fluorine, chlorine or bromine atom or a $C_{1-4}$ alkyl group;

$R^3$ represents a hydrogen atom or, when both $Y^1$ and $y^2$ represent N, may also represent a $C_{1-4}$ alkyl or hydroxymethyl group;

$R^4$ represents a hydrogen atom or, when Z represents N, $R^4$ may also represent a $C_{1-4}$ alkyl group;

$R^5$ represents a $C_{1-4}$ alkyl or phenyl $C_{1-4}$ alkyl group;

$R^6$ represents a hydrogen atom or a $C_{1-4}$ alkyl group.)

However, the compounds in the above application is disclosed as platelet aggregation inhibitor. GPIIb/IIIa antagonists having wide safety range and a definite effect through oral administration are highly desired.

DISCLOSURE OF THE INVENTION

The present inventors created novel benzamidine derivatives of the following formula and found that the derivatives have excellent GPIIb/IIIa antagonizing activity, and filed a patent application (Japanese patent application No. Hei-8-333342(kokai).

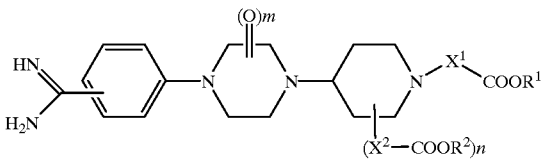

(wherein $R^1$ and R are the same or different and each represents a hydrogen atom or an ester residue;

$X^1$ represents a lower alkylene group;

$X^2$ represents a single bond or a lower alkylene group;

m represents 0, 1, or 2;

n represents 0 or 1, provided that n=1 when m=0.).

As a result of further extensive studies, it was found that novel substituted-amidinobenzene derivatives obtained by changing these amidinobenzene derivatives to prodrugs at the amidino group have extremely excellent peroral absorbability and sustainment of the effect, resulting in accomplishment of the present invention.

Thus, the present invention relates to the substituted-amidinobenzene derivatives of the following general formula (I) and their salts, as well as pharmaceutical compositions comprising such compounds along with pharmaceutically acceptable carriers.

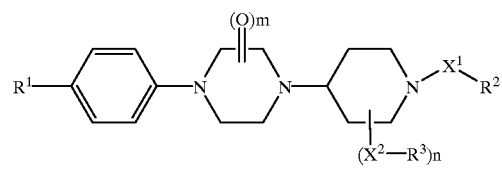

(the symbols in the above formula have the following meanings:

$R^1$: a group which can be converted into an amidino group in vivo;

$R^2$ and $R^3$: the same or different and each represents a carboxyl group or a group which can be converted into a carboxyl group in vivo;

$X^1$ and $X^2$: the same or different and each represents a lower alkylene group;

m: 0, 1 or 2;

n: 0 or 1, provided that n=1 when m=0. The same applies hereinafter.)

The compounds of the present invention are structurally characterized in that the substituent $R^1$ on benzene is a group which can be converted into an amidino group in vivo and thus the compounds are prodrugs. As described below, such change into prodrugs achieved extremely excellent peroral absorbability and accompanying sustained effects. The second characteristics is that (1) the compounds have two carboxyl group or group which can be converted into a carboxyl group in vivo on the piperidine ring and/or (2) the compounds have one or two oxo groups on the piperazine ring. The compounds of the present invention have excellent GPIIb/IIIa antagonizing effect based on such a structure.

Preferable compounds among the compounds of the present invention in the general formula (I) shown above are:

the substituted-amidinobenzene derivatives or salts thereof, wherein at least one of $R^2$ and $R^3$ is a group which can be converted into a carboxyl group in vivo (i.e., the compounds which have been made into prodrugs at both of the amidino group and the carboxyl group (so-called double prodrug compounds));

the substituted-amidinobenzene derivatives or salts thereof, wherein the group which can be converted into an amidino group in vivo of $R^1$ is a group selected from the group consisting of a hydroxyamidino group, a lower alkoxycarbonylamidino group, a lower alkoxyamidino group and a lower alkanoylamidino group;

the substituted-amidinobenzene derivatives or salts thereof, wherein the group which can be converted into an carboxyl group in vivo of $R^2$ and $R^3$ is a group selected from the group consisting of a lower alkoxycarbonyl group, a lower alkoxy-lower alkoxycarbonyl group, a lower alkoxy-lower alkoxy-lower alkoxycarbonyl group, a halogeno-lower alkoxylcarbonyl group, a lower alkenyloxycarbonyl group, a lower alkanoyloxy-lower alkoxycarbonyl group, a lower alkenoyloxy-lower alkoxycarbonyl group, a lower alkanoyl-lower alkoxycarbonyl group, a lower alkenoyl-lower alkoxycarbonyl group, a lower alkoxy-lower alkanoyloxy-lower alkoxycarbonyl group, a lower alkoxycarbonyloxy-lower alkoxycarbonyl group, a lower alkoxy-lower alkoxycarbonyloxy-lower alkoxycarbonyl group, di-lower alkylamino-lower alkoxycarbonyl group, a cycloalkyloxycarbonyloxy-lower alkoxycarbonyl group, a lower alkoxybenzyloxycarbonyl group, a nitrobenzyloxycarbonyl group, a lower alkoxybenzhydryloxycarbonyl group, a benzhydryloxycarbonyl group, a benzoyloxy-lower alkoxycarbonyl group, a 2-oxotetrahydrofuran-5-yloxycarbonyl group, a 2-oxo-5-alkyl-1,3-dioxolen-4-ylmethoxycarbonyl group, a tetrahydrofuranylcarbonyloxymethoxycarbonyl group, and a 3-phthalidyloxycarbonl group; and the substituted-amidinobenzene derivatives or salts thereof, wherein m=1.

Still preferable compounds are the substituted-amidinobenzene derivatives or salts thereof, wherein m=1 and n=0.

Particularly preferable compounds are the compounds shown below or salts thereof.

Ethyl 4-[4-(4-hydroxylamidinophenyl)-3-oxo-1-piperazinyl]-1-piperidineacetate, methyl 4-[4-(4-hydroxylamidinophenyl)- 3-oxo-1-piperazinyl]-1-piperidineacetate, ethyl 4-[4-(4- methoxycarbonylamidinophenyl)-3-oxo-1-piperazinyl]-1-piperidineacetate, methyl 4-[4-(4-methoxycarbonylamidinophenyl)-3-oxo-1-piperazinyl]-1-piperidineacetate, and ethyl 4-[4-(4-ethoxycarbonylamidinophenyl)-3-oxo-1-piperazinyl]-1-piperidineacetate. Among these compounds, the most preferable compound is ethyl 4-[4-(4-hydroxylamidinophenyl)-3-oxo-1-piperazinyl]-1-piperidineacetate or salts thereof.

Other preferable compounds include the substituted-amidinobenzene derivatives or salts thereof, wherein m=0 and n=1, particularly the substituted-amidinobenzene derivatives or salts thereof wherein both of $R^2$ and $R^3$ are a group which can be converted into a carboxyl group in vivo.

Hereinafter, the compounds (I) of the present invention are described in detail.

Unless otherwise specifically indicated, the term "lower" as referred to herein for the definitions of the general formulae given herein is directed to a linear or branched carbon chain having from 1 to 6 carbon atoms.

Accordingly, the "lower alkylene group" represented by $X^1$ and $X^2$ in the general formula (I) is suitably a linear or branched alkylene group having from 1 to 6 carbon atoms, and its illustrative examples include a methylene group, an ethylene group, a methylmethylene group, a trimethylene group, a propylene group, a 2-propylene group, a dimethylmethylene group, a tetramethylene group, a 1-methyltrimethylene group, a 2-methyltrimethylene group, a 3-methyltrimethylene group, a 1-ethylethylene group, a 2-ethylethylene group, a 2,2-dimethylethylene group, a 1,1-dimethylethylene group, an ethylmethylmethylene group, a propylmethylene group, a pentamethylene group, a 1-methyltetramethylene group, a 2-methyltetramethylene group, a 3-methyltetramethylene group, a 4-methyltetramethylene group, a 1,1-dimethyltrimethylene group, a 2,2-dimethyltrirethylene group, a 3,3-dimethyltrimethylene group, a 1,3-dimethyltrimethylene group, a 2,3-dimethyltrimethylene group, a 1,2-dimethyltrimethylene group, a 1-ethyltrimethylene group, a 1,1,2-trimethylethylene group, a diethylmethylene group, a 1-propylethylene group, a 2-propylethylene group, a butylmethylene group, a hexamethylene group, a 1-methylpentamethylene group, a 1,1-dimethyltetramethylene group, a 2,2-dimethyltetramethylene group, a 3,3-dimethyltetramethylene group, a 4,4-dimethyltetramethylene group, a 1,1,3-trimethyltrimethylene group, a 1,1,2-trimethyltrimethylene group, a 1,1,2,2-tetramethylethylene group, a 1,1-dimethyl-2-ethylethylene group, a 1,1-diethylethylene group, a 1-propyltrimethylene group, a 2-propyltrimethylene group, a 3-propyltrimethylene group, a 1-butylethylene group, a 2-butylethylene group, a 1-methyl-1-propylethylene group, a 2-methyl-2-propylethylene group, a 1-methyl-2-propylethylene group, a 2-methyl-propylethylene group, a pentylmethylene group, a butylmethylmethylene group, an ethylpropylmethylene group, and the like. Among these groups, straight alkylene groups of 1 to 3 carbon atoms are preferable, and a methylene group and an ethylene group are the most preferable.

The "group which can be converted into an amidino group in vivo" of $R^1$ and the "group which can be converted into a carboxyl group in vivo" of $R^2$ and/or $R^3$ are the groups which constitute the compound which can be an active body of medicines, or a group constituting an amidine prodrug which can be metabolized in vivo to become an amidine compound as an active body in the former case or a group constituting a carboxylic acid prodrug which can be metabolized in vivo to form a carboxylic acid compound as an active body in the letter case.

The "group which can be converted into an amidino group in vivo" and the "group which can be converted into a carboxyl group in vivo" can be easily determined by administering the compound of the present invention to human or other animals and analyzing the metabolized product by ordinary analytical techniques. That is, the former can be detected as a compound having an amidino group after metabolism in vivo and the latter can be detected as a compound having a carboxyl group after metabolism in vivo.

Accordingly, the "group which can be converted into an amidino group in vivo" of $R^1$ includes substituted amidino groups which can be hydrolyzed by metabolism in vivo, i.e., those constituting an amidino group-based prodrug. The substituted amidino group include a hydroxyamidino group, a lower alkoxycarbonylamidino group, a lower alkoxyamidino group and a lower alkanoylamidino group. A hydroxyamidino group and a lower alkoxycarbonylamidino group are preferable, and a hydroxyamidino group is particularly preferable.

The "group which can be converted into a carboxyl group in vivo" of $R^2$ and/or $R^3$ includes substituted carboxyl groups which can be hydrolyzed by metabolism in vivo, i.e., those constituting a carboxyl group-based prodrug. The substituted carboxyl group include an unsubstituted lower alkoxy-carbonyl group and straight-chain substituted lower alkoxycarbonyl groups, e.g., a lower alkoxy-lower alkoxycarbonyl group, a lower alkoxy-lower alkoxy-lower alkoxycarbonyl group, a halogeno-lower alkoxylcarbonyl group, a lower alkenyloxycarbonyl group, a lower alkanoyloxy-lower alkoxycarbonyl group, a lower alkenoyloxy-lower alkoxycarbonyl group, a lower alkanoyl-lower alkoxycarbonyl group, a lower alkenoyl-lower alkoxycarbonyl group, a lower alkoxy-lower alkanoyloxy-lower alkoxycarbonyl group, a lower alkoxycarbonyloxy-lower alkoxycarbonyl group, a lower alkoxy-lower alkoxycarbonyloxy-lower alkoxycarbonyl group, and di-lower alkylamino-lower alkoxycarbonyl group, and a cycloalkyloxycarbonyloxy-lower alkoxycarbonyl group, a lower alkoxybenzyloxycarbonyl group, a nitrobenzyloxycarbonyl group, a lower alkoxybenzhydryloxycarbonyl group, a benzhydryloxycarbonyl group, a benzoyloxy-lower alkoxycarbonyl group, a 2-oxotetrahydrofuran-5-yloxycarbonyl group, a 2-oxo-5-alkyl-1,3-dioxolen-4-ylmethoxycarbonyl group, a tetrahydrofuranylcarbonyloxymethoxycarbonyl group, and a 3-phthalidyloxycarbonl group. Preferable groups are an unsubstituted lower alkoxycarbonyl group and the straight-chain substituted lower alkoxycarbonyl groups, e.g., a lower alkoxy-lower alkoxycarbonyl group, a lower alkoxy-lower alkoxy-lower alkoxycarbonyl group, a halogeno-lower alkoxylcarbonyl group, a lower alkenyloxycarbonyl group, a lower alkanoyloxy-lower alkoxycarbonyl group, a lower alkenoyloxy-lower alkoxycarbonyl group, a lower alkanoyl-lower alkoxycarbonyl group, a lower alkenoyl-lower alkoxycarbonyl group, a lower alkoxy-lower alkanoyloxy-lower alkoxycarbonyl group, a lower alkoxycarbonyloxy-lower alkoxycarbonyl group, a lower alkoxy-lower alkoxycarbonyloxy-lower alkoxycarbonyl group, and di-lower alkylamino-lower alkoxycarbonyl group, and a cycloalkyloxycarbonyloxy-lower alkoxycarbonyl group, a 2-oxo-5-alkyl-1,3-dioxolen-4-ylmethoxycarbonyl group, and a 3-phthalidyloxycarbonl group. A lower alkoxycarbonyl group is more preferable, and a methoxycarbonyl group and an ethoxycarbonyl group are particularly preferable.

The "lower alkyl group" includes, for example, a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, and the like.

The "lower alkoxy group" corresponds to a hydroxyl group of which a hydrogen atom is substituted by the above-described lower alkyl group, such as a methoxy group, an ethoxy group, a propoxy group, an isopropoxy group, a butoxy group, an isobutoxy group, a sec-butoxy group, a tert-butoxy group, a pentyloxy (amyloxy) group, an isopentyloxy group, a tert-pentyloxy group, a neopentyloxy group, a 2-methylbutoxy group, a 1,2-dimethylpropoxy group, a 1-ethylpropoxy group, a hexyloxy group, and the like, preferably a methoxy group, an ethoxy group, and a tert-butoxy group.

The "lower alkanoyl group" is preferably those having 2 to 6 carbon atoms (e.g., acetyl, propionyl, pivaloyl, and the like); the "lower alkenoyl group" is preferably those having 3 to 6 carbon atoms (an acryloyl group, a crotonoyl group, a maleoyl group, and the like); the "cycloalkyl group" is preferably those having 3 to 8 carbon atoms, particularly those having 3 to 6 carbon atoms (e.g., cyclopropyl, cyclopentyl, cyclohexyl, and the like).

The "lower alkenyl group" is preferably those having from 2 to 6 carbon atoms (e.g., a vinyl group, an allyl group, a 1-propenyl group, and the like).

The "halogeno-lower alkyl group" corresponds to the above-mentioned lower alkyl group of which one or more hydrogen atoms is/are substituted by halogen atom(s) and includes a fluoromethyl group, a chloromethyl group, a bromomethyl group, an iodomethyl group, a 1-chloroethyl group, a 2-chloroethyl group, a dichloromethyl group, a trifluoromethyl group, a dichlorobromomethyl group, and the like.

In the basic skeleton of the compound (I) of the present invention, the moiety represented by the formula

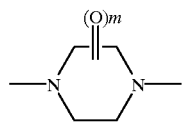

means an oxopiperazine ring or a dioxopiperazine ring.

The illustrative examples of the oxopiperazine ring according to the present application are shown below.

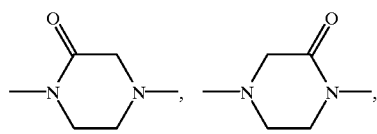

-continued

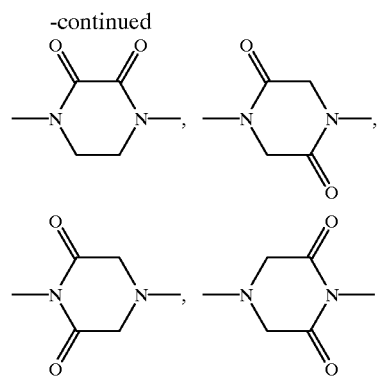

Among these rings, the ring represented by

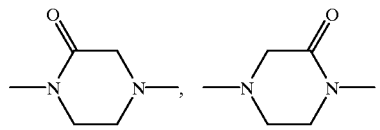

is preferably and the ring represented by

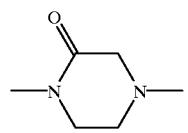

is particularly preferable.

The compounds (I) of the present invention have at least one asymmetric carbon atom, depending on the skeletal piperidinyl group and its substituent (a group of $-X^2-R^3$). Depending on the other substituents, the compounds (I) may have additional asymmetric carbon atom(s). The compounds of the present invention may exist in the form of optical isomers, depending on these asymmetric carbon atoms. In addition, they exist in the form of tautomeric isomers depending on the carbonyl groups or the amidino groups in the substituents and also in the form of geometric isomers depending on the double bonds. The present invention encompasses all isolated isomers of these optical isomers, tautomeric isomers, and geometric isomers as well as their mixtures.

The compounds (I) of the present invention may be formed into salts. Examples of the preferred salts include alkali metal or alkaline earth metal salts such as sodium salts, potassium salts, and calcium salts; hydrogen halides such as hydrofluorides, hydrochlorides, hydrobromides, and hydroiodides; salts with inorganic acids, such as carbonates, nitrates, perchlorates, sulfates, and phosphates; lower alkylsulfonates such as methanesulfonates, trifluoromethanesulfonates, and ethanesulfonates; arylsulfonates such as benzenesulfonates and p-toluenesulfonates; salts with organic acids, such as fumarates, succinates, citrates, tartrates, oxalates, and maleates; salts with amino acids, such as glutamates and aspartates.

In addition, the present invention also encompasses hydrates and pharmaceutically acceptable solvates of compounds (I) as well as polymorphic isomers of the compounds (I) of the present invention. As a matter of course, the present invention is not limited to only the compounds of the Examples to be mentioned hereinafter but encompasses all substituted-amidinobenzene derivatives of the general formula (I) and their pharmaceutically acceptable salts.

(Production Methods)

Some typical production methods for the compounds of the present invention are explained below. First Production Method

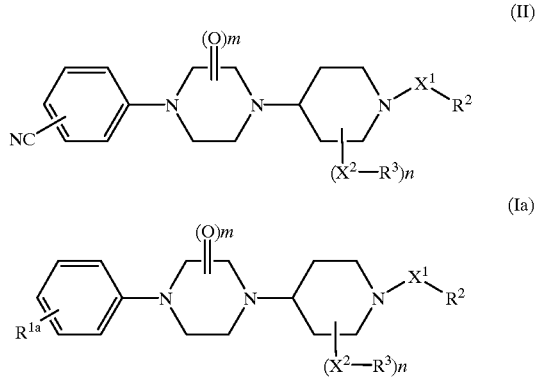

(In the formula, $R^2$, $R^3$, $X^1$, $X^2$, m and n have the same meanings as above. $R^{1a}$ means a hydroxyamidino group (or a lower alkoxy amidino group).

The compound (Ia) of the present invention can be produced by reacting the nitrile compound (II) with hydroxylamine hydrochloride (or a lower alkoxyamine hydrochloride) in an appropriate solvent in the presence of a base. The appropriate solvent is preferably those inert to the reaction and examples of such inert solvents include methanol, ethanol, dimethylformamide (DMF), dimethylacetamide, tetrachloroethane, dichloromethane, dichloroethane, chloroform, carbon tetrachloride, tetrahydrofuran (THF), dioxane, dimethoxymethane, diethoxymethane, ethyl acetate, benzene, toluene, acetonitrile, dimethylsulfoxide (DMSO), etc., and mixed solvents thereof. The solvent is appropriately selected depending on the various reaction conditions.

Examples of the base include sodium, sodium hydride, sodium methoxide, sodium ethoxide, potassium carbonate, triethylamide, pyridine, and the like. Examples of the base preferably used in this reaction include triethylamine, sodium methoxide, and sodium ethoxide.

The reaction may be carried out normally under room temperature, with heating, or with heating under reflux, and preferably with heating under reflux.

Second Production Method

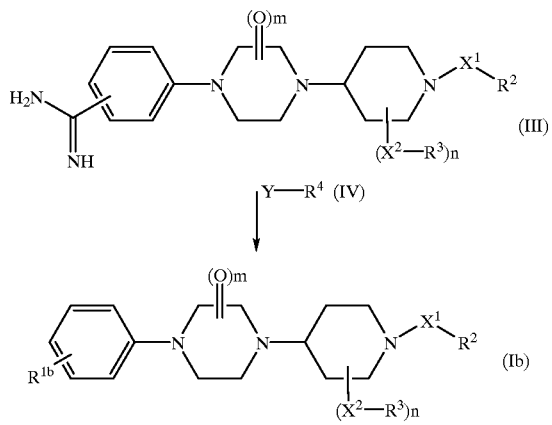

(In the formula, $R^2$, $R^3$, $X^1$, $X^2$, m and n have the same meanings as above. $R^4$ means a lower alkoxycarbonyl groups (or a lower alkanoyl group). $R^{1b}$ means a lower alkoxycarbonylamidino group (or a lower alkanoyl amidino group). Y means a releasable group such as a halogen atom, a hydroxyl group, a lower alkoxy group, a phenoxy group, an imidazolyl group, an arylsulfonyloxy group, and a leaving group of an active carboxylic acid derivative.)

The compound (Ib) of the present invention can be produced by reacting the amidino compound (III) with a compound (IV) in the presence of an appropriate base. Examples of the appropriate base include those described above, and preferably sodium hydroxide, potassium carbonate, and triethylamine. Solvents may be used in this reaction and, examples of the solvents to be used include those described above. Examples of the preferable solvents include layered solvent of water-dichloromethane, THF, DMF, and the like.

The active carboxylic acid derivative includes active esters to be obtained by the reaction with a phenol compound such as p-nitrophenol or the like, or with an N-hydroxyamine compound such as N-hydroxysuccinimide, 1-hydroxy-benzotriazole or the like; mixed acid anhydrides to be obtained by the reaction with a monoalkyl carbonate or an organic acid, and mixed phosphoryl anhydrides to be obtained by reaction with diphenylphosphoryl chloride and N-methylmorpholine; acid azides to be obtained by reacting an ester with hydrazine or an alkyl nitrite; acid halides such as acid chlorides, acid bromides, etc.; symmetric acid anhydrides, etc.

(Other Production Methods)

Among the compounds (I) of the present invention, those having a carboxyl group as $R^2$ and/or $R^3$ can be obtained by dissolving the corresponding compounds having a group which can be converted into a carboxyl group in vivo as $R^2$ and/or $R^3$, in an appropriate solvent followed by ordinary hydrolysis of ester under basic conditions, acidic conditions or neutral conditions.

Examples of the base to be used under basic conditions include sodium hydroxide, potassium hydroxide, lithium hydroxide, barium hydroxide, and the like. Examples of the acid to be used under acidic conditions include Lewis acids (e.g., hydrochloric acid, sulfuric acid, boron trichloride), trifluoroacetic acid, p-toluenesulfonic acid. Under neutral conditions, halogen ions (e.g., lithium iodide and lithium bromide), alkali metal salts (e.g., thiol and selenol), iodotrimethylsilane, and enzymes (e.g., esterase) may be used.

Examples of the solvent to be used in the reaction include water, alcohol (e.g., methanol and ethanol), acetone, dioxane, acetonitrile, tetrahydrofuran, N,N-dimethylformamide, dimethylsulfoxide, formic acid, acetic acid, pyridine, lutidine, collidine, and the like. The above-described commonly used solvents may be used as a mixture with water.

The reaction normally proceeds under room temperature but sometimes should be carried out under ice-cooling or with heating, and thus the reaction is carried out under the appropriately selected temperature.

Selecting the conditions for the hydrolysis appropriately, substituted-carboxylic acid compounds having only one carboxyl group. For example, an ester compound in which one ester residue is easily hydrolyzed under acidic conditions (for example, tert-butyl group or the like) and the other ester residue is easily hydrolyzed under basic conditions (for example, methyl ester, ethyl ester or the like) is hydrolyzed under selected conditions (acidic or basic conditions), whereby only one of the two ester residues is selectively hydrolyzed.

If desired, carboxylic acid compounds can further be esterified to give desired esters. The esterification can be effected in any ordinary manner under suitably selected conditions.

Compounds of the present invention where $R^2$ and/or $R^3$ are/is the group which can be converted into a carboxyl group in vivo can also be obtained by interesterification with suitable alcohols. For example, a large excess amount of an alcohol is used for the interesterification to be carried out in the presence of an acid or a base or any other catalyst (for example, titanium (IV) alkoxide) or the other alcohols to be formed during the reaction are removed out of the reaction system, thereby shifting the equilibrium of the reaction toward the system of producing the desired ester compound.

(Methods for Producing Compounds of Starting Compounds)

Next, methods for preparing the compounds to be used as starting compounds are described below.

Production Method A

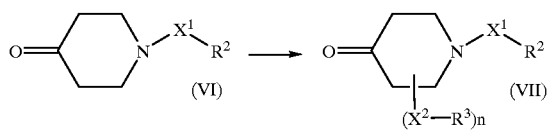

(In the formula, $R^3$, $R^4$, $X^1$, and $X^2$ have the same meanings as mentioned above.)

The compound (VII) may be obtained by dissolving a compound (VI) in an appropriate solvent followed by reaction with an appropriate secondary amine to give an enamine, and then allowing alkyl acrylate (e.g., methyl acrylate) or halogenated alkyl (e.g., ethyl bromoacetate) to act on the enamine. The enamine may be used after isolation or without isolation.

Examples of the secondary amine include pyrrolidine, piperidine, morpholine, diethylamine, and diisopropylamine.

Examples of the solvent include toluene, benzene, chlorobenzene, and the like. In addition to these commonly used solvents, the reaction may be carried out in any other organic solvents as long as the solvent does not cause bad influence on the reaction.

The reaction is carried out with removing water out of the system which is formed when enamine is formed, by adding water-absorbing agents such as potassium hydroxide, Molecular Sieves, etc. or by using Dean-Stark Trap (azeotropic dehydrate apparatus). The temperature for the reaction is preferably set to azeotropic or reflux temperature.

Production Method B

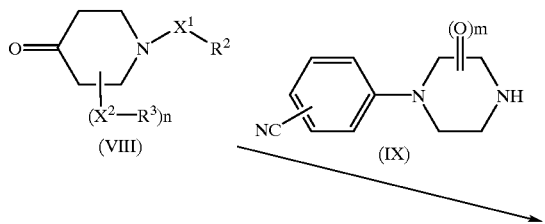

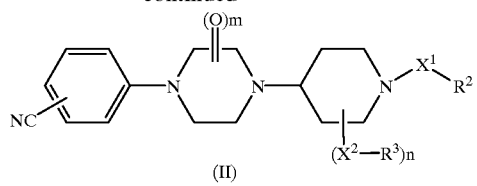

(In the formula, $R^3$, $R^4$, $X^1$, $X^2$, m and n have the same meanings as above.)

The compound (II) is obtained by dissolving a compound (VIII) in a suitable solvent followed by reacting it with an amine compound (IX) to give a Schiff base, which is then reduced after isolation or without isolation.

The solvent is an organic solvent inert to the reaction, including, for example, benzene, toluene, xylene, methanol, ethanol, isopropanol, methylene chloride, dichloroethane, chloroform, acetic acid, and the like.

The reaction is conducted in such a way that a compound (VIII) is reacted with a reaction-corresponding amount of an amine compound (IX) or, alternatively, using one of them in a somewhat excessive amount, preferably in the presence of an acid catalyst such as p-toluenesulfonic acid, adipic acid, oxalic acid, pyridine hydrochloride, acetic acid or the like. Depending on the reaction conditions, the reaction is advantageously carried out with removing water out of the system, by adding water-absorbing agents such as potassium hydroxide, Molecular Sieves, etc. or by using Dean-Stark Trap (azeotropic dehydrate apparatus). The temperature for the reaction is usually under room temperature but may be set to azeotropic or reflux temperature depending on the reaction conditions.

The reduction of Schiff base is carried out by adding a reducing agent such as a metal hydride complex (e.g., sodium borohydride, lithium borohydride, sodium cyanoborohydride, and sodium triacetoxyborohydride), borane, or the like in a former step reaction solution.

Production Method C

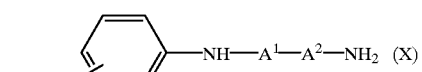
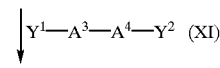
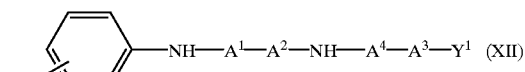

(In the formula, $A^1$ to $A^4$ may be the same or different and each is a carbonyl group or a methylene group; $Y^1$ represents the same releasable group as Y, and $Y^2$ represents is the same leaving group as $Y^1$ or a hydrogen atom.)

In this reaction, a compound (XI) is reacted with an amine compound (X) to produce a compound (XII). (1) When the compound (XI) above is an alkyl derivative wherein $Y^2$ is a leaving group, and $A^4$ is a methylene group.

This reaction may be carried out according to ordinary N-alkylation. The reaction is carried out by stirring an amine compound (X) and a reaction-corresponding amount of a compound (XI) in an inert solvent with cooling or under heating. To promote the reaction, it is desirable to add a base (for example, an inorganic base such as potassium carbonate, sodium carbonate, sodium hydride or the like, or an organic base such as triethylamine or the like) to the reaction system.

(2) When the compound (XI) above is a carboxylic acid derivative wherein $Y^2$ is a leaving group, and $A^4$ is a carbonyl group The amide compound (XII) is obtained by acylating an amine (X) with a carboxylic acid or its active derivative (XI) in a suitable solvent.

The active carboxylic acid derivative includes active esters described above in Second Production Method and an amide compound (XII) is also obtained by acylation in the a carboxylic acid (XI) and a condensing agent in a suitable solvent. The condensing agent to be used in the reaction is preferably N,N-dicyclohexylcarbodiimide (DCC), 1-ethyl-3-(3-(N,N-dimethylamino)propyl)carbodiimide, carbonyldiimidazole, diphenylphosphorylazide (DPPA), diethylphosphorylazide or the like.

The reaction is usually carried out in a solvent under cooling or room temperature. The solvent to be used is organic solvents which do not participate in the reaction, such as dimethylformamide, dimethylacetamide, dioxane, tetrahydrofuran, diethyl ether, dichloroethane, chloroform, carbon tetrachloride, dimethoxymethane, dimethoxyethane, ethyl acetate, benzene, acetonitrile, dimethyl sulfoxide, etc., and mixed solvents thereof. These organic solvents may be appropriately selected depending on the method to be applied. Depending on the type of acylation, the reaction should sometimes be carried out under dehydrated conditions. In addition, depending on the method to be applied, it is preferable for the smooth progress of the reaction to carry out the reaction in the presence of a base such as N-methylmorpholine, triethylamide, trimethylamine, pyridine, etc. or by using such a base as a solvent.

(3) When the compound (XI) above is an aldehyde wherein $Y^2$ is a hydrogen atom, and $A^4$ is a carbonyl group.

A compound (XII) is obtained by dissolving an aldehyde derivative (XI) in a suitable solvent, reacting it with an amine (X) and thereafter reducing the iminium ion produced. The reaction solvent, the reducing agent and the reaction conditions in the above-mentioned Production Method B may be applied to this reaction.

Production Method D

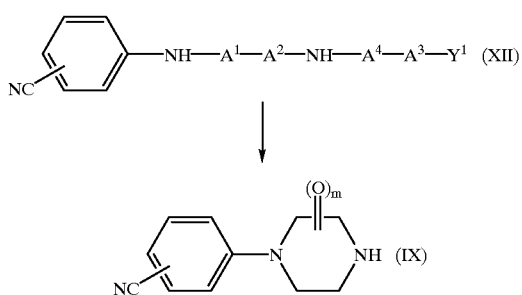

(In the formula, $A^1$ to $A^4$, $Y^1$, and m have the same meanings as above.)

To obtain a (di)oxopiperazine ring compound (IX) by cyclization, the precursor (XII) is treated in a suitable solvent in the absence or presence of a suitable catalyst. This reaction is carried out with ice-cooling or at room temperature or under heating.

Examples of the solvents to be used include dimethylformamide, dimethylacetamide, dimethylsulfoxide, tetrachloroethane, dichloromethane, dichloroethane, chloroform, carbon tetrachloride, tetrahydrofuran, dioxane, dimethoxymethane, dimethoxyethane, benzene, chlorobenzene, toluene, water, acetic anhydride, alcohols, etc., which are appropriately selected depending on the various reaction conditions.

Examples of the catalyst to be used include bases (e.g., sodium hydride, potassium hydride, n-butyllithium, sec-butyllithium, potassium tert-butoxide, potassium bis(trimethylsilyl)amide, lithium diisopropylamide, sodium methoxide, sodium ethoxide, sodium hydroxide, potassium hydroxide, potassium carbonate, potassium hydrogencarbonate, sodium carbonate, sodium hydrogencarbonate, triethylamine, diisopropylethylamine, dimethylaminopyridine), salts (e.g., sodium acetate and potassium acetate), and acids (e.g., sulfuric acid and hydrochloric acid).

Production Method E

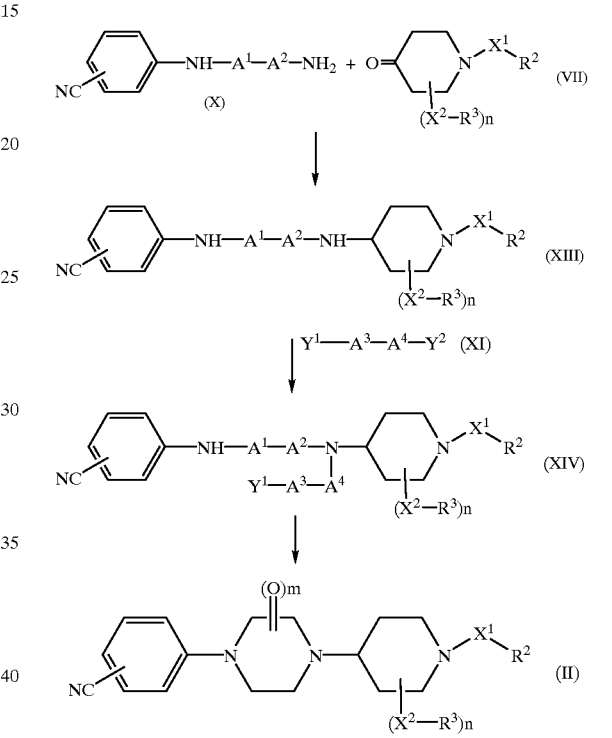

(In the formula, $A^1$ to $A^4$, $X^1$, $X^2$, $Y^1$, $Y^2$, $R^2$, $R^3$, m and n have the same meanings as above.)

In the similar manner as described in Production Method B, the compound (X) and the compound (VII) are reacted to form a compound (XIII), The solvent, catalyst, and the reaction conditions, etc. are the same with those of the above-described Production Method B.

In the similar manner as described in Production Method C, the compound (XIV) is produced from the compound (XIII). The solvent, catalyst, and the reaction conditions, etc. are the same with those of the above-described Production Method C.

Cyclization to form (di)oxopiperazine ring can be carried out in the same manner described in the Production Method D. The solvent, catalyst, and the reaction conditions, etc. are the same with those of the above-described Production Method D.

Production Method F

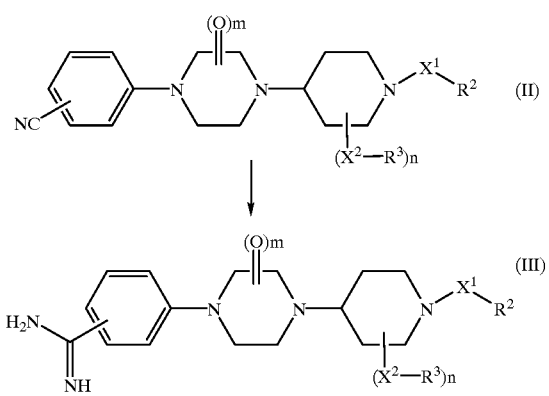

(In the formula, $R^2$, $R^3$, $X^1$, $X^2$, m, and n have the same meanings as above.)

Compounds (III) having an amidino group can be produced according to any of the following methods (i), (ii) and (iii).

(i) Method of Converting a Nitrile into an Imidate Followed by Condensing with an Amine:

A nitrile compound (II) is reacted with an alcohol such as methanol, ethanol or the like in the presence of a hydrogen chloride gas at from −40° C. to 0° C. to give an imidate, which is then reacted with ammonia or an amine or amine salt such as ammonium carbonate, ammonium chloride, ammonium acetate or the like. As the solvent for the reaction, methanol, ethanol, acetone, tetrahydrofuran, or the like is used.

(ii) Method of Converting a Nitrile into a Thioamide and then into a Thioimidate Followed by Condensing with an Amine:

A nitrile compound (II) is reacted with hydrogen sulfide in the presence of an organic base such as methylamine, triethylamine, pyridine, picoline or the like to give a thioamide compound. The thioamide compound can also be obtained by reacting a nitrile compound (II) with O,O-diethyl dithiophosphate in the presence of hydrogen chloride.

The thus-obtained thioamide compound is then reacted with a lower alkyl halide such as methyl iodide, ethyl iodide or the like to give a thioimidate, which is then reacted with ammonia or an amine or amine salt such as ammonium carbonate, ammonium chloride, ammonium acetate or the like. As the solvent for the reaction, methanol, ethanol, acetone, tetrahydrofuran, ethyl acetate, or the like is used.

(iii) Method of Directly Adding an Amine, Amine Salt, Metal Amide or Grignard Reagent to a Nitrile:

A reagent such as ammonia, ammonium chloride with ammonia, ammonium thiocyanate, alkylammonium thiocyanate, MeAl(Cl)NH$_2$, NaNH$_2$, (CH$_3$)$_2$NMgBr or the like is added to a nitrile compound (II) in an appropriate solvent or without solvent. As the solvent, chloroform, methanol, ethanol, acetone, tetrahydrofuran, toluene, dimethylformamide, or the like is used. Addition of a catalyst of a base such as sodium hydride or the like or an acid such as aluminium chloride, p-toluenesulfonic acid or the like to the reaction system noticeably accelerates the reaction in some cases. The reaction may be carried out with cooling, or at room temperature, or under heating.

Production Method G

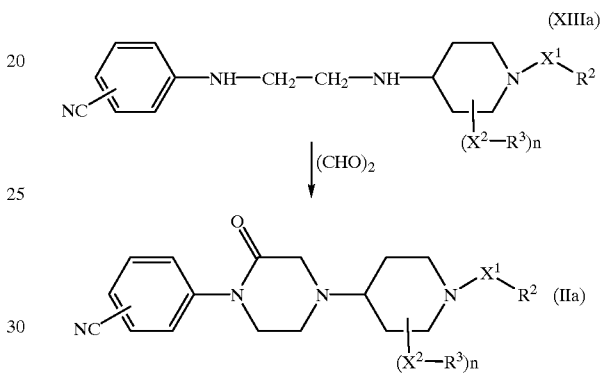

(In the Formula, $R^2$, $R^3$, $X^1$, $X^2$, and n have the same meanings as above)

The cyclization to form an oxopiperazine ring compound (IIa) is carried out by reacting a precursor (XIIIa) with glyoxal in an appropriate solvent.

The reaction may be carried out with ice-cooling, under room temperature, or under heating.

Examples of the solvent to be used include mixed solvent of tetrahydrofuran-water, dimethylformamide, dimethyl sulfoxide, 1-methyl-2-pyrrolidine, dioxane, dimethoxymethane, alcohols, etc., which may be selected appropriately depending on the various reaction conditions.

Production Method H

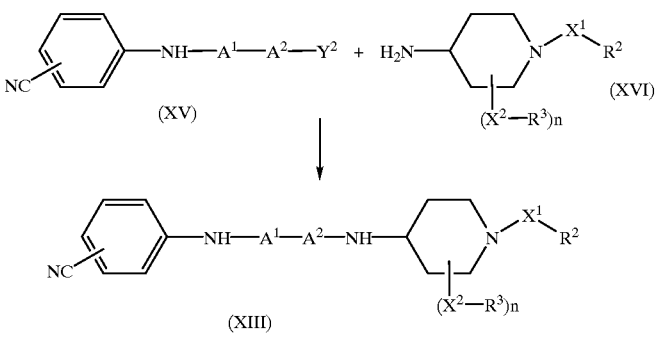

(In the formula, $A^1$, $A^2$, $X^1$, $X^2$, $Y^2$, $R^2$, $R^3$ and n have the same meanings as above)

This reaction process is to obtain the compound (XIII) by reacting the compound (XV) and the amine compound (XVI).

1) When $Y^2$ is $Y^1$ and $A^2$ is a methylene group in the compound (XV) above, the reaction is carried out in the similar manner as described in 1) of Production Process C.

2) When $Y^2$ is $Y^1$ and $A^2$ is a carbonyl group in the compound (XV) above, the reaction is carried out in the similar manner as described in 2) of Production Process C.

3) When $Y^2$ is a hydrogen atom and $A^2$ is a carbonyl group in the compound (XV) above, the reaction is carried out in the similar manner as described in 3) of Production Process C.

The compounds of the present invention as produced in the manner mentioned above are isolated and purified by any ordinary chemical operation which includes, for example, extraction, precipitation, fractional chromatography, recrystallization, and the like. In addition, the compounds of the present invention can be led into desired salts by ordinary salt-forming reaction.

Industrial Applicability

The compounds of the present invention are useful as orally-applicable GPIIb/IIIa receptor antagonists, especially platelet aggregation inhibitor, including, for example, medicines for ameliorating ischemic cardiac disorders (anxiety stenocardia, acute myocardial infarction), and also for prevention of the following secondary complications, postoperative re-obstruction and re-stenosis following coronary artery bypass or PTCA, as well as for promotion of coronary thrombolysis and prophylaxis of re-obstruction following coronary thrombolysis, etc.); as adminicula in cardiosurgery operations or in vascular surgery operations; as medicines for ameliorating cerebrovascular disorders (transient ischemic attack (TIA), cerebral infarction, subarachnoid hemorrhage (vascular twitch), etc.); and as medicines for ameliorating peripheral artery disorders (chronic arterial obstruction, etc.).

Since the compounds of the present invention have especially useful as a prodrug of compounds in our previous application (an unexamined published Japanese patent application No. 8-333342) and are therefore useful as medicines for ameliorating the above-mentioned disorders not only by parenteral administration such as, for example, intravascular injection but also by peroral administration. In addition, since plasma residence time of Compound A is prolonged by the administration of the compounds of the present invention as a prodrug, the pharmaceutical effects of the compounds of the present invention is long acting, and the clinical usefulness of the compounds is high. Moreover, the toxicity of the compounds of the present invention is much lower than that of conventional compounds.

The platelet aggregation-inhibiting effect of the compounds of the present invention and usefulness as the prodrug have been confirmed by the following test methods:

Metabolic Test of an Active Body (Compound A) in Plasma

Compound of Example 2 of the present invention was administered to three beagle dogs orally at a dose of 10 mg/kg as an aqueous solution and then blood was withdrawn over 48 hours after administration. After centrifugation, plasma was separated and then stored at −20° C. until analysis. Compound A (compound name: 4-[4-(4-amidinophenyl)-3-oxo-1-piperazinyl]-1-piperidineacetic acid, an unexamined published Japanese patent application No. 8-333342), which is an active body produced as a metabolite of Compound of Example 2, was determined by the high performance liquid chromatography method to obtain the pharmacokinetic parameters. Compound A was also administered to the same beagle dogs at a dose of 10 mg/kg, and then plasma Compound A concentration was measured. Pharmacokinetic parameters of Compound A after the administration of Compound of Example 2 and Compound A were compared-with each other. In Table 1 it is shown the pharmacokinetic parameters of plasma Compound A after oral administration, and in FIG. 1 it is shown the plasma concentration-time profile of Compound A after oral administration.

Table 1 represents Pharmacokinetic parameters of plasma Compound A after oral administration of Compound of Example 2 and Compound A to beagle dogs at a dose of 10 mg/kg (mean of three animals±standard deviation) and FIG. 1 represents plasma concentration-time profile of Compound A.

TABLE 1

| Drug | $C_{max}$ (ng/ml) | $T_{max}$ (hr) | $AUC_{0-48}$ (ng · hr/ml) | $t_{1/2}$ (hr) |
|---|---|---|---|---|
| Compound of Example 2 | 532 ± 29 | 5.3 ± 1.2 | 13535 ± 459 | 19.6 ± 1.8 |
| Compound A | 748 ± 175 | 1.7 ± 0.6 | 3550 ± 838 | 2.1 ± 0.0 |

(where $C_{max}$ is the maximum plasma concentration, $T_{max}$ is the time to reach $C_{max}$, $AUC_{0-48}$ is the area under the time-concentration curve in plasma over 48 hours after administration, $t_{1/2}$ is the elimination half life.)

The area under the time-concentration curve in plasma of Compound A after the administration of Compound of Example 2 was over 3 times higher than that after the administration of Compound A. The $t_{1/2}$ of Compound A also greatly prolonged when it was orally administered as Compound of Example 2. It is confirmed that not only bioavailability but also plasma residence time of Compound A increase when it is administered as Compound of Example 2 which is designed for a double prodrug of Compound A.

Ex Vivo Platelet Aggregation-Inhibiting Activity in Cynomolgus Monkeys

Cynomolgus monkeys that had been lightly anesthetized by intramuscular administration of ketamine hydrochloride were fixed on a work-bench, and a sample compound of the present invention dissolved or suspended in a methylcellulose solution was administered into the stomach via a stomach tube at a dose of 1 mg/kg. Before the administration and after the administration at a predetermined period of time, 3 ml (containing 1/10 times by volume of sodium citrate) of the blood was collected from the animal through the femoral vein. From the blood, platelet-rich-plasma (PRP) was obtained according to the method of De Marco et al's (see J. clin. Invest., 77, 1272–1277, 1986). The PRP was adjusted at 3×10⁸/ml with an automatic blood cell counter (MEK-5158 Model, produced by Nihon Koden Co.) before use. Then, 20 μM of ADP and 10 μg/ml of bovine tendon-derived collagen (produced by Niko Bioscience Co.) as triggers to cause the aggregation of the platelets. The degree of the aggregation of the platelets was measured with a platelet aggregation meter (NBS Hematracer 801, produced by Niko Bioscience Co.). The platelet aggregation-inhibiting activity of the tested compound was represented by the inhibition percentage (%) relative to the maximum aggregation percentage of each animal before the addition of the test compound.

The test results are shown in Table 2 together with the results of the Compound A which is the active body of the compounds of the present invention.

TABLE 2

| | | Platelet aggregation-inhibiting ratio | | | | |
| --- | --- | --- | --- | --- | --- | --- |
| Compound | n | after 3 hours | after 6 hours | after 9 hours | after 12 hours | after 24 hours |
| Compound A | 6 | 19.7 ± 9.4 | 16.3 ± 7.5 | 14.2 ± 5.9 | ND | ND |
| Example 2 | 3 | 24.7 ± 23.7 | 66.3 ± 15.4 | 88.0 ± 11.0 | 89.0 ± 4.6 | 54.0 ± 9.0 |
| Example 7 | 3 | 9.0 ± 5.7 | 42.0 ± 14.7 | 60.0 ± 15.6 | 64.3 ± 8.7 | 26.0 ± 2.9 |

(ND: no data)

As shown in the above results, the compounds of the present invention showed excellent platelet aggregation-inhibiting ratio even in comparison with the active body compound A. In addition, the platelet aggregation-inhibiting ratio in the case of the prodrug compound of the present application was excellently maintained after 9, 12, and 24 hours after the administration, which confirmed that the compound shows sufficient sustainment of the effect.

Incidentally, as described in our previous application, the active body compound in the present application has excellent effect to inhibit binding of GPIIb/IIIa to fibrinogen and thus it per se has platelet aggregation-inhibiting effect. Accordingly, it is clear that the compounds of the present invention, after absorption in viva, is metabolized to become active body compound shown above as the results of metabolic test of an active body in plasma and shows platelet aggregation-inhibiting effect based on the effect to inhibit binding of fibrinogen to GPIIb/IIIa.

As shown in the above pharmacological test results, the compounds of the present invention are excellent in bioavailability and in sustainment of the effect. Accordingly, it was confirmed that the compounds of the present invention are favorable-compounds as a prodrug, especially as a double prodrug.

Pharmaceutical compositions comprising one or more of the compounds and their salts of the present invention as the active ingredient can be formulated along with carriers, excipients and other additives which are generally used in ordinary formulation.

The carriers and excipients to be used for the formulation may be solid or liquid, non-toxic pharmaceutically acceptable substances. Examples of such carriers and excipients include lactose, magnesium stearate, starch, talc, gelatin, agar, pectin, gum arabic, olive oil, sesame oil, cacao butter, ethylene glycol and others which are ordinarily used in the art.

The pharmaceutical composition can be administered either orally as tablets, pills, capsules, granules, powders, liquids, etc., or parenterally as intravenous or intramuscular injections, suppositories, transdermal preparations, inhalants, intracystic injection, etc. The dose of the composition is suitably determined for individual patients, depending on their conditions, ages, sexes, etc. In general, however, the oral dose to adults is approximately from 0.01 mg/kg/day to 100 mg/kg/day, which is administered once at a time or in from 2 to 4 portions. Where the composition is administered intravascularly depending on the conditions of patients, the dose is, in general, approximately from 0.001 mg/kg to 10 mg/kg and is applied once to several times a day.

The solid composition for use in the oral administration according to the present invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone, metasilicic acid or magnesium aluminate. In the usual way, the composition may contain additives other than the inert diluent, such as a lubricant (e.g., magnesium stearate), a disintegrating agent (e.g., calcium cellulose glycolate), a stabilizing agent (e.g., lactose) and a solubilization-assisting agent (e.g., glutamic acid and aspartic acid). If necessary, tablets or pills may be coated-with a film of a gastric or enteric substance such as sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a commonly used inert diluent such as purified water or ethyl alcohol. In addition to the inert diluent, this composition may also contain auxiliary agents such as a moistening agent, a suspending agent and the like, as well as sweeteners, flavors, aromas and antiseptics.

The injections for parenteral administration includes aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, a plant oil (e.g., olive oil), an alcohol (e.g., ethyl alcohol), Polysorbate 80 and the like. Such a composition may further contain additive agents such as an antiseptic, a moistening agent, an emulsifying agent, a dispersing agent, a stabilizing agent (e.g., lactose) and a solubilization assisting agent (e.g., glutamic acid and aspartic acid). These compositions are sterilized by filtration through a bacteria-retaining filter, blending of a germicide or irradiation. Alternatively, they may be used by making into sterile solid compositions and dissolving them in sterile water or a sterile solvent for injection prior to their use.

BEST MODES OF CARRYING OUT THE INVENTION

The present invention is described in more detail by means of the following Examples. However, the compounds of the present invention are not limited to only the compounds of the Examples but include all the compounds of the above-mentioned general formula (I), their salts, hydrates, solvates, tautomers, geometric and optical isomers and polymorphic isomers.

Reference Example 1

Methyl 4-oxo-3-piperidinecarboxylate hydrochloride (9.65 g), 21.0 g of ethyl bromoacetate and 24.0 g of potassium carbonate were dissolved in 200 ml of N,N-dimethylformamide and the solution was stirred at room temperature overnight. Then, 100 ml of water was added to the reaction liquid, and the mixture was extracted with 500 ml of ethyl acetate. The resulting extract was dried over sodium sulfate and concentrated. The resulting residue was purified by silica gel column chromatography (eluent: chloroform) to give 9.0 g of ethyl 3-ethoxycarbonylmethyl-3-methoxycarbonyl-4-oxo-1-piperidineacetate as an oily substance.

Mass spectrum (m/z): FAB (Pos) 330 (M$^+$+1)

NMR spectrum (CDCl$_3$, TMS internal standard): δ: 1.23–1.31 (6H, m), 2.46–2.51 (1H, m), 2.71 (2H, dd), 2.91–2.96 (2H, m), 3.00–3.08 (2H, m), 3.35–3.45 (2H, m), 3.79 (3H, s), 4.10–4.19 (4H, m)

Reference Example 2

Ethyl 3-ethoxycarbonylmethyl-3-methoxycarbonyl-4-oxo-1-piperidineacetate (1.0 g) and 140 mg of lithium chloride were dissolved in 10 ml of N,N-dimethylformamide and the solution was refluxed for 48 hours. Then, 10 ml of water was added to the reaction liquid, and the mixture was extracted with 100 ml of ethyl acetate. The resulting extract was dried over sodium sulfate and concentrated. The resulting residue was purified by silica gel column chromatography (eluent: chloroform) to give 400 mg of diethyl 4-oxo-1,3-piperidinediacetate as an oily substance.

Mass spectrum (m/z): FAB (Pos.) 272 (M$^+$+1)

NMR spectrum (CDCl$_3$, TMS internal standard): δ: 1.23–1.30 (6H, m), 2.18 (1H, dd), 2.36–2.40 (1H, m), 2.50 (1H, t), 2.70–2.77 (3H, m), 3.13–3.26 (3H, m), 3.38 (2H, s), 4.09–4.22 (4H, m)

Reference Example 3

Diethyl 4-oxo-1,3-piperidinediacetate (28 g), 19 g of 4-(1-piperazinyl)benzonitrile and 6 g of acetic acid were dissolved in 250 ml of dichloromethane, 42 g of sodium triacetoxyborohydride was added, and the mixture was stirred at room temperature for 24 hours. The reaction liquid was neutralized with an aqueous 1 N sodium hydroxide solution and then the organic layer was separated. The organic layer was dried over sodium sulfate and concentrated, and the resulting residue was purified by silica gel chromatography (eluent: hexane:ethyl acetate=1:1) to give 13 g of diethyl 4-[4-(4-cyanophenyl)-1-piperazinyl]-1,3-piperidineacetate.

Reference Example 4

Diethyl 4-[4-(4-cyanophenyl)-1-piperazinyl]-1,3-piperidineacetate (8.2 g) was dissolved in 100 ml of ethanol, and hydrogen chloride was made to blown at from −10° C. to −20° C. until saturation. The solution was heated to room temperature and stirred overnight, and the solvent was removed by evaporation. The residue thus obtained was dissolved in 100 ml of ethanol, 9.0 g of ammonium carbonate was added, and the mixture was stirred at room temperature overnight. The solvent was removed from the reaction mixture by evaporation, and the resulting residue was purified by silica gel column chromatography (eluent: chloroform:methanol =10:1) to give 4.4 g of diethyl 4-[4-(4-amidinophenyl)-1-piperazinyl]-1,3-piperidineacetate hydrochloride.

Mass spectrum (m/z): FAB (Pos.) 460 (M$^+$+1)

NMR spectrum (DMSO-d$_6$, TMS internal standard): δ: 1.18 (6H, t), 1.69–1.83 (3H, m), 2.01–2.33 (5H, m), 2.66–2.87 (3H, m), 3.08–3.23 (4H, m), 4.03–4.33 (4H, m), 7.06 (2H, d), 7.73 (2H, d)

Reference Example 5

N-(tert-Butoxycarbonyl)glycine (14.83 g) was dissolved in 50 ml of tetrahydrofuran, and 13.73 g of 1,1'-carbonylbis-1H-imidazole was gradually added, and the mixture was stirred at room temperature for 3 hours. Then, 10 g of p-aminobenzonitrile was added and the mixture was stirred for 3 days. Then, the solvent was removed by evaporation under a reduced pressure. Water was added to the resulting residue. The crystals thus formed were collected by filtration, washed with a small amount of ethanol, and then dried under a reduced pressure to give 20.5 g of 2-(tert-butoxycarbonylamino)-N-(4-cyanophenyl)acetamide.

Mass spectrum (m/z): FAB 276 (M+H)$^+$

NMR spectrum (CDCl$_3$, TMS internal standard): δ: 1.49 (9H, s), 3.92 (2H, d), 5.18 (1H, brs), 7.61 (2H, d), 7.65 (2H, d), 8.59 (1H, brs)

Reference Example 6

An ethyl acetate solution (45.5 ml) of 4N hydrogen chloride solution was added to 10 g of 2-(tert-butoxycarbonylamino)-N-(4-cyanophenyl)acetamide in a closed vessel and the mixture was stirred for 18 hours. The crystals formed were collected by filtration, washed with ethyl acetate and then dried under a reduced pressure to give 7.7 g of 2-amino-N-(4-cyanophenyl)acetamide hydrochloride. Then, 58.8 ml of an aqueous saturated sodium hydrogencarbonate solution and 20 ml of water were added to 3.7 g of the hydrochloride thus obtained, and the mixture was stirred for 1 hour. The crystals thus formed were collected by filtration and dried under a reduced pressure to give 2.5 g of 2-amino-N-(4-cyanophenyl)acetamide.

Mass spectrum (m/z): FAB 176 (M+H)$^+$

NMR spectrum (CDCl$_3$, TMS internal standard): δ: 1.68 (2H, brs), 3.50 (2H, s), 7.61 (2H, d), 7.74 (2H, d), 9.75 (1H, brs)

Reference Example 7

2-Amino-N-(4-cyanophenyl)acetamide (1.83 g) was dissolved in 90 ml of methylene chloride, 3.10 g of ethyl 2-(4-oxo-1-piperidine)acetate, 4.4 ml of acetic acid and 8.88 g of sodium triacetoxyborohydride were added in that order, and the mixture was stirred for 1.5 hours. After concentrating the mixture under a reduced pressure, water and sodium carbonate were added to make the system alkaline. Then, the crystals formed were collected by filtration. The crude crystals were dissolved in chloroform and washed with brine. The resulting organic layer was dried over anhydrous sodium sulfate and filtered, and the resulting filtrate was concentrated under a reduced pressure. Ether was added to the resulting residue, and the solid formed was collected by filtration to give 2.82 g of ethyl 4-[N-(4-cyanophenyl) carbamoylmethylamino]-1-piperidineacetate.

Mass spectrum (m/z): APCI+QlMS: 345

NMR spectrum (CDCl$_3$, TMS internal standard): δ: 1.27 (3H, t), 1.50–1.58 (2H, m), 1.67 (1H, brs), 1.88–1.90 (2H, m), 2.23–2.27 (2H, m), 2.49–2.54 (1H, m), 2.95 (2H, m), 3.22 (2H, s), 3.42 (2H, s), 4.18 (2H, q), 7.62 (2H, d), 7.72 (2H, d), 9.69 (1H, brs)

Reference Example 8

Sodium cyanoborohydride (0.48 g) and 0.57 g of acetic acid were added in that order to a mixed solution of 1.0 g of ethyl 4-[N-(4-cyanophenyl)carbamoylmethylamino]-1-piperidineacetate, 10 ml of methanol and 2.85 g of chloroacetaldehyde (40% aqueous solution), and the mixture was stirred overnight. The solvent was removed by evaporation, chloroform was added, and the mixture was washed with an aqueous saturated sodium hydrogencarbonate solution. The resulting organic layer was separated and concentrated under a reduced pressure. The resulting residue was subjected-to silica gel column chromatography (eluent: chloroform:methanol=100:1, v/v) to give 1.15 g of ethyl 4-[N-(2-chloroethyl)-N-[N-(4-cyanophenyl) carbamoylmethyl]amino]-1-piperidineacetate.

Mass spectrum (m/z): FAB 407 (M+H)+

Reference Example 9

Ethyl 4-[N-(2-chloroethyl)-N-[N-(4-cyanophenyl) carbamoylmethyl]amino]-1-piperidineacetate (1.08 g) was dissolved in 30 ml of N,N-dimethylformamide, 0.18 g of sodium hydride (60% in oil) was gradually added, and the mixture was stirred for 5 hours. An aqueous saturated ammonium chloride solution was added, and the solvent was removed by evaporation. Then, chloroform and an aqueous saturated sodium hydrogencarbonate solution were added, the mixture was subjected to liquid-liquid separation, and the resulting organic layer was concentrated under a reduced pressure. Ether was added to the resulting residue, and the solid formed was collected by filtration to give 0.43 g of ethyl 4-[4-(4-cyanophenyl)-3-oxo-1-piperazinyl]-1-piperidineacetate.

Mass spectrum (m/z): FAB 371 (M+H)+

NMR spectrum (CDCl$_3$, TMS internal standard): δ: 1.28 (3H, t), 1.65–1.71 (2H, m), 1.83–1.85 (2H, m), 2.24–2.28 (2H, m), 2.35–2.39 (1H, m), 2.91–2.93 (2H, m), 3.01–3.04 (2H, m), 3.22 (2H, s), 3.46 (2H, s), 3.71–3.73 (2H, m), 4.19 (2H, q), 7.49 (2H, d), 7.68 (2H, d)

In the same manner as in Reference Example 4, the compound of the following Reference Example 10 was obtained.

Reference Example 10

Ethyl 4-[4-(4-amidinophenyl)-3-oxo-1-piperazinyl]-1-piperidineacetate hydrochloride Starting compound: Ethyl 4-[4-(4-cyanophenyl)-3-oxo-5 1-piperazinyl]-1-piperidineacetate Mass spectrum (m/z): FAB 388 (M+H)+

NMR spectrum (DMSO-d$_6$, TMS internal standard): δ: 1.19 (3H, t), 1.43–1.47 (2H, m), 1.77–1.80 (2H, m), 2.17–2.21 (2H, m), 2.29 (1H, m), 2.87–2.89 (4H, m), 3.19 (2H, s), 3.33 (2H, s), 3.70–3.72 (2H, d), 4.08 (2H, q), 7.65 (2H, d), 7.84 (2H, d), 9.01 (2H, brs), 9.32 (2H, brs)

In the same manner as in Reference Example 9, the compound of the following Reference Example 11 was obtained.

Reference Example 11

Methyl 4-[4-(4-cyanophenyl)-3-oxo-1-piperazinyl]-1-piperidineacetate

Starting compound: Methyl 4-[N-(2-chloroethyl)-N-[N-(4-cyanophenyl)carbamoylmethyl]amino]-1-piperidineacetate Mass spectrum (m/z): FAB (Pos.) 357 (M++1)

NMR spectrum (CDCl$_3$, TMS internal standard): δ: 1.63–1.73 (2H, m), 1.83–1.86 (2H, m), 2.22–2.28 (2H, m), 2.33–2.41 (1H, m), 2.91–2.93 (2H, m), 3.00–3.03 (2H, m), 3.24 (2H, s), 3.46 (2H, s), 3.71–3.74 (5H, m), 7.49 (2H, d), 7.68 (2H, d)

In the same manner as in Reference Example 4, the compound of the following Reference Example 12 was obtained.

Reference Example 12

Methyl 4-[4-(4-amidinophenyl)-3-oxo-1-piperazinyl]-1-piperidineacetate hydrochloride Starting compound: Methyl 4-[4-(4-cyanophenyl)-3-oxo-1-piperazinyl]-1-piperidineacetate Mass spectrum (m/z): FAB (Pos.) 374 (M++1)

NMR spectrum (DMSO-d$_6$, TMS internal standard): δ: 1.47 (2H, m), 1.79–1.81 (2H, m), 2.21–2.31 (3H, m), 2.89 (4H, m), 3.34 (4H, m), 3.62 (3H, s), 3.71–3.73 (2H, m), 7.65 (2H, d), 7.88 (2H, d), 9.28 (2H, brs), 9.43 (2H, brs)

Reference Example 13

Ethyl 4-[[2-(4-cyanoanilino)ethyl]amino]-1-piperidineacetate (1.0 g) was dissolved in a mixed solvent of 10 ml of tetrahydrofuran and 10 ml of water, 0.69 ml of glyoxal (40%, aqueous) was added, and the mixture was stirred at room temperature for 15 hours. The solvent was evaporated and the residue was extracted with ethyl acetate. The organic layer was washed successively with an aqueous saturated sodium hydrogencarbonate solution and brine. The organic layer was dried over anhydrous magnesium sulfate and the solvent was evaporated. The resulting crude crystals were recrystallized from toluene-hexane to give 0.86 g of ethyl 4-[4-(4-cyanophenyl)-3-oxo-1-piperazinyl]-1-piperidineacetate.

Mass spectrum (m/z): FAB 371 (M+H)+

NMR spectrum (CDCl$_3$, TMS internal standard): δ: 1.28 (3H, t), 1.5–1.9 (4H, m), 2.1–2.4 (3H, m), 2.9–3.1 (4H, m), 3.22 (2H, s), 3.46 (2H, s), 3.7–3.8 (2H, m), 4.19 (2H, q), 7.48 (2H, d), 7.69 (2H, d)

EXAMPLE 1

Hydroxylamine hydrochloride (700 mg) was dissolved in 100 ml of ethanol and 680 mg of sodium ethoxide was added at room temperature. After 5 minutes, 2.2 g of (±)-cis-diethyl 4-[4-(4-cyanophenyl)-1-piperazinyl]-1,3-piperidineacetate was added, and the mixture was refluxed overnight. The reaction solution was concentrated, 200 ml of water was added, and the mixture was extracted with 300 ml of chloroform. The extract was dried over sodium sulfate, concentrated, and then purified by silica gel column chromatography (eluent: chloroform:methanol=50:1 to 20:1) to give 1.5 g of (±)-cis -diethyl 4-[4-(4-hydroxyamidinophenyl)-1-piperazinyl]-1,3-piperidineacetate.

Mass spectrum (m/z): FAB (Pos.) 476 (M++1)

NMR spectrum (CDCl$_3$, TMS internal standard): δ: 1.24–1.28 (6H, m), 1.76–1.78 (1H, m), 2.06–2.11 (1H, m), 2.21–2.30 (2H, m), 2.55–2.75 (7H, m), 4.06–4.22 (4H, m), 4.80 (2H, s), 6.88 (2H, d), 7.51 (2H, d)

EXAMPLE 2

Ethanol (38 ml), 0.90 g of Hydroxylamine hydrochloride, and 1.64 g of triethylamine were added to 3.0 g of ethyl 4-[4-(4-cyanophenyl)-3-oxo-1-piperazinyl]-1-piperidineacetate, and the mixture was heated under reflux for 3 hours. The crystals formed were collected by filtration at the temperature of about 30° C, and recrystallized from chloroform-ethanol to give 2.27 g of ethyl 4-[4-(4-hydroxyamidinophenyl)-3-oxo-1-piperazinyl]-1-piperidineacetate Elemental analysis (for $C_{20}H_{29}N_5O_4$) C (%) H (%) N (%) Calcd. 59.54 7.24 17.36 Found 59.31 7.05 17.32

NMR spectrum (DMSO-d$_6$, TMS internal standard): δ: 1.19 (3H, t), 1.39–1.48 (2H, m), 1.77–1.80 (2H, m), 2.16–2.21 (2H, m), 2.24–2.27 (1H, m), 2.83–2.89 (4H, m), 3.19 (2H, s), 3.28 (2H, s), 3.62–3.65 (2H, m), 4.08 (2H, q), 5.81 (2H, s), 7.34 (2H, d), 7.67 (2H, d), 9.64 (1H, s)

In the same manner as in Example 1, the compound of the following Example 3 was obtained.

EXAMPLE 3

Methyl 4-[4-(4-hydroxyamidinophenyl)-3-oxo-1-piperazinyl]-1-piperidineacetate

Starting compound: Methyl 4-[4-(4-cyanophenyl)-3-oxo-1-piperazinyl]-1-piperidineacetate Elemental analysis (for $C_{19}H_{27}N_5O_4 \cdot 0.25\ H_2O$) C (%) H (%) N (%) Calcd. 56.63 7.13 17.38 Found. 56.81 6.79 17.26

NMR spectrum ($CDCl_3$, TMS internal standard): δ: 1.73–1.86 (4H, m), 2.22–2.28 (2H, m), 2.34–2.41 (1H, m), 2.87–2.89 (2H, m), 3.02–3.05 (2H, m), 3.25 (2H, s), 3.45 (2H, s), 3.62–3.65 (2H, m), 3.73 (3H, s), 4.83 (2H, brs), 7.32 (2H, d), 7.62 (2H, d)

EXAMPLE 4

(±)-cis-Diethyl 4-[4-(4-hydroxyamidinophenyl)-1-piperazinyl]-1,3-piperidinediacetate (1.5 g) was dissolved in 50 ml of 1N hydrochloric acid and the solution was refluxed overnight. The reaction liquid was concentrated and the concentrate was purified by ODS column chromatography (eluent: water to water:methanol=1:1) to give 100 mg of (±)-cis-4-[4-(4-hydroxyamidinophenyl)-1-piperazinyl]-1-[(ethoxycarbonyl)methyl]piperidine-3-acetic acid trihydrochloride.

Mass spectrum (mtz): FAB (Pos.) 448 ($M^+ + 1$)

NMR spectrum (DMSO-$d_6$, TMS internal standard): δ: 1.18 (3H, t), 1.76 (1H, m), 1.98–2.01 (1H, m), 2.10–2.19 (2H, m), 4.06 (2H, q), 5.62 (2H, s), 6.89 (2H, d), 7.51 (2H, d), 9.33 (1H, s)

EXAMPLE 5

(±)-cis-Diethyl 4-[4-(4-hydroxyamidinophenyl)-1-piperazinyl]-1,3-piperidinediacetate (1.5 g) was dissolved in 50 ml of 1N hydrochloric acid and the solution was refluxed overnight. The reaction liquid was concentrated and the concentrate was purified by ODS column chromatography (eluent: water) to give 450 mg of (±)-cis-4-[4-(4-hydroxyamidinophenyl)-1,3-piperidinediacetic acid trihydrochloride.

Mass spectrum (m/z): FAB (Pos.) 420 ($M^+ + 1$)

NMR spectrum (DMSO-$d_6$, TMS internal standard): δ: 7.15 (2H, d), 7.71 (2H, d), 11.09 (1H, s)

EXAMPLE 6

(±)-cis-Diethyl 4-[4-(4-amidinophenyl)-1-piperazinyl]-1,3-piperidinediacetate hydrochloride (1.5 g) was dissolved in 150 ml of methylene chloride, 300 mg of methyl chloroformate and 30 ml of a 0.2N aqueous sodium hydroxide solution were added, and the mixture was stirred at room temperature for 1 hour. The organic layer was separated, washed twice with water, dried over sodium sulfate, and then concentrated. The resulting residue was purified by silica gel column chromatography (eluent: chloroform:methanol=50:1) to give 850 mg of (±)-cis-diethyl 4-[4-(4-methoxycarbonylamidinophenyl)-1-piperadinyl]-1,3-piperidinediacetate.

Mass spectrum (m/z): FAB (Pos.) 518 ($M^+ + 1$)

NMR spectrum ($CDCl_3$, TMS internal standard): δ: 1.24–1.28 (6H, m), 1.47–1.59 (3H, m), 1.77 (1H, d), 2.06–2.11 (1H, m), 2.21–2.30 (2H, d), 2.54–2.60 (3H, m), 2.63–2.71 (4H, m), 2.88–2.95 (2H, m), 3.17 (2H, q), 3.28 (4H, t), 3.78 (3H, s), 4.06–4.19 (4H, m), 6.87 (2H, d), 7.81 (2H, d)

In the same manner as in Example 6, the compound of the following Example 7 were obtained.

EXAMPLE 7

Ethyl 4-[4-(4-methoxycarbonylamidinophenyl)-3-oxo-1-piperazinyl]-1-piperidineacetate Starting compound: Ethyl 4-(4-(4-amidinophenyl)-3-oxo-1-piperazinyl]-1-piperidineacetate

| Elemental analysis (for $C_{22}H_{31}N_5O_5$) | | | |
|---|---|---|---|
| | C (%) | H (%) | N (%) |
| Calcd. | 59.31 | 7.01 | 15.72 |
| Found | 59.02 | 7.03 | 15.63 |

NMR spectrum ($CDCl_3$, TMS internal standard): δ: 1.28 (3H, t), 1.63–1.75 (2H, m), 1.83–1.86 (2H, m), 2.22–2.28 (2H, m), 2.33–2.41 (1H, m), 2.90–2.92 (2H, m), 3.01–3.04 (2H, m), 3.23 (2H, s), 3.45 (2H, s), 3.69–3.72 (2H, m), 3.78 (3H, s), 4.19 (2H, q), 7.40 (2H, d), 7.90 (2H, d)

EXAMPLE 8

Ethyl 4-[4-(4-hydroxyamidinophenyl)-3-oxo-1-piperazinyl]-1-piperidineacetate (0.8 g) was dissolved in 8 ml of water, and 0.21 g of lithium hydroxide monohydrate was added with ice-cooling. The mixture was stirred for 30 minutes with ice-cooling, an aqueous saturated ammonium chloride solution was added, and the mixture was concentrated. The crystals formed were collected by filtration to give 0.67 g of 4-[4-(4-hydroxyamidinophenyl)-3-oxo-1-piperazinyl]-1-piperidineacetic acid.

| Elemental analysis (for $C_{18}H_{25}N_5O_4 \cdot H_2O$) | | | |
|---|---|---|---|
| | C (%) | H (%) | N (%) |
| Calcd. | 54.95 | 6.92 | 17.80 |
| Found | 55.14 | 6.66 | 18.00 |

NMR spectrum (DMSO-$d_6$+$CF_3COOD$, TMS internal standard): δ: 2.11–2.14 (2H, m), 2.38 (2H, m), 3.17 (2H, m), 3.64–3.77 (5H, m), 4.04–4.07 (2H, m), 4.18 (4H, m), 7.65 (2H, d), 7.83 (2H, d)

In the same manner as in Example 6, the compounds of the following Examples 9 to 10 were obtained.

EXAMPLE 9

Methyl 4-[4-(4-methoxycarbonylamidinophenyl)-3-oxo-1-piperazinyl]-1-piperidineacetate Starting compound: Methyl 4-[4-(4-amidinophenyl)-3-oxo-1-piperazinyl]-1-piperidineacetate hydrochloride

| Elemental analysis (for $C_{21}H_{29}N_5O_5 \cdot 0.25\ H_2O$) | | | |
|---|---|---|---|
| | C (%) | H (%) | N (%) |
| Calcd. | 57.85 | 6.82 | 16.06 |
| Found | 57.70 | 6.60 | 16.20 |

NMR spectrum (CDCl₃, TMS internal standard): δ: 1.63–1.73 (2H, m), 1.83–1.86 (2H, m), 2.22–2.28 (2H, m), 2.34–2.40 (1H, m), 2.89–2.92 (2H, m), 3.00–3.03 (2H, m), 3.24 (2H, s), 3.45 (2H, s), 3.70–3.72 (2H, m), 3.73 (3H, s), 3.78 (3H, s), 7.40 (2H, d), 7.90 (2H, d)

EXAMPLE 10

Ethyl 4-[4-(4-ethoxycarbonylamidinophenyl)-3-oxo-1-piperazinyl]-1-piperidineacetate Starting compound: Ethyl 4-[4-(4-amidinophenyl)-3-oxo-1-piperazinyl]-1-piperidineacetate hydrochloride

| Elemental analysis (for $C_{23}H_{33}N_5O_5 \cdot 0.25\ H_2O$) | | | |
|---|---|---|---|
| | C (%) | H (%) | N (%) |
| Calcd. | 59.53 | 7.28 | 15.09 |
| Found | 59.61 | 7.13 | 15.08 |

NMR spectrum (CDCl₃, TMS internal standard): δ: 1.28 (3H, t), 1.35 (3H, t), 1.63–1.73 (2H, m), 1.83–1.86 (2H, m), 2.23–2.28 (2H, m), 2.34–2.40 (1H, m), 2.90–2.92 (2H, m), 3.01–3.04 (2H, m), 3.23 (2H, s), 3.45 (2H, s), 3.70–3.73 (2H, m), 4.17–4.25 (4H, m), 7.43 (2H, d), 7.91 (2H, d)

The chemical structures of the compounds obtained in the Examples above are set forth following Table 3 and Table 4.

TABLE 3

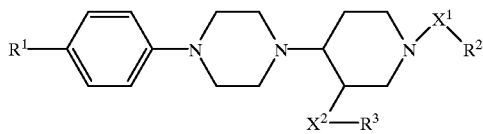

| Ex. No. | R¹ | X¹ | R² | X² | R³ | sal. |
|---|---|---|---|---|---|---|
| 1 | HO—N=C(NH₂)– (amidoxime) | CH₂ | —COOC₂H₅ | CH₂ | —COOC₂H₅ | — |
| 4 | HO—N=C(NH₂)– | CH₂ | —COOC₂H₅ | CH₂ | —COOH | 3HCl |
| 5 | HO—N=C(NH₂)– | CH₂ | —COOH | CH₂ | —COOH | 3HCl |
| 6 | CH₃O–C(O)–NH–C(=NH)– | CH₂ | —COOC₂H₅ | CH₂ | —COOC₂H₅ | — |

TABLE 4

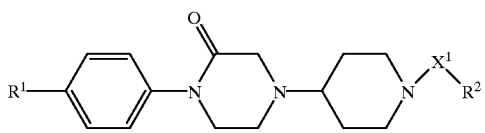

| Ex. No. | R¹ | X¹ | R² |
|---|---|---|---|
| 2 | HO—N=C(NH₂)– | CH₂ | —COOC₂H₅ |
| 3 | HO—N=C(NH₂)– | CH₂ | —COOCH₃ |
| 7 | CH₃O–C(O)–NH–C(=NH)– | CH₂ | —COOC₂H₅ |

TABLE 4-continued

[Structure: R¹-(4-phenyl)-N-piperazinone-N-piperidine-N-X¹-R²]

| Ex. No. | R¹ | X¹ | R² |
|---|---|---|---|
| 8 | HO-N=C(CH₃)-NH₂ (hydroxyamidine with NH₂) | CH₂ | —COOH |
| 9 | CH₃O-C(=O)-NH-C(CH₃)=NH (methoxycarbonyl amidine) | CH₂ | —COOCH₃ |
| 10 | C₂H₅O-C(=O)-NH-C(CH₃)=NH (ethoxycarbonyl amidine) | CH₂ | —COOC₂H₅ |

In addition to the above-described compounds of examples, other compounds of the present invention are shown in the following Table 5 through Table 9. These compounds can be synthesized, without particular experiments, in accordance with any one of the above-described in Production Methods and Processes and modified processes thereof known to those ordinary skilled in the art.

TABLE 5

[Structure: R¹-(4-phenyl)-A-piperidine-N-X¹-R²]

| No. | R¹- | -A- | -X¹- | -R² |
|---|---|---|---|---|
| 1 | HO-N=C(CH₃)-NH₂ | 2-oxopiperazine-1,4-diyl | —CH₂— | —COOC₂H₅ |
| 2 | HO-N=C(CH₃)-NH₂ | 2,3-dioxopiperazine-1,4-diyl | —CH₂— | —COOC₂H₅ |
| 3 | HO-N=C(CH₃)-NH₂ | 2,5-dioxopiperazine-1,4-diyl | —CH₂— | —COOC₂H₅ |
| 4 | HO-N=C(CH₃)-NH₂ | 2,6-dioxopiperazine-1,4-diyl | —CH₂— | —COOC₂H₅ |

TABLE 5-continued

| No. | R¹- | -A- | -X¹- | -R² |
|---|---|---|---|---|
| 5 | HO-N=C(CH₃)-NH₂ (hydroxyamidine) | 2,3-dioxopiperazine-1,4-diyl | —CH₂— | —COOC₂H₅ |
| 6 | C₂H₅O-C(=O)-NH-C(=NH)- | 2-oxopiperazine-1,4-diyl | —CH₂— | —COOC₂H₅ |
| 7 | C₂H₅O-C(=O)-NH-C(=NH)- | 2,3-dioxopiperazine-1,4-diyl | —CH₂— | —COOC₂H₅ |
| 8 | C₂H₅O-C(=O)-NH-C(=NH)- | 2,5-dioxopiperazine-1,4-diyl | —CH₂— | —COOC₂H₅ |
| 9 | C₂H₅O-C(=O)-NH-C(=NH)- | 2,6-dioxopiperazine-1,4-diyl | —CH₂— | —COOC₂H₅ |
| 10 | C₂H₅O-C(=O)-NH-C(=NH)- | 2,3-dioxopiperazine-1,4-diyl | —CH₂— | —COOC₂H₅ |

TABLE 6

| No. | R¹- | -X¹- | -R² |
|---|---|---|---|
| 11 | HO-N=C(CH₃)-NH₂ | —CH₂— | —OC(=O)-CH(CH₃)-O-C(=O)-OC₂H₅ |

TABLE 6-continued
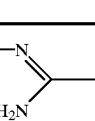
| No. | R¹- | -X¹- | -R² |
|---|---|---|---|
| 12 | 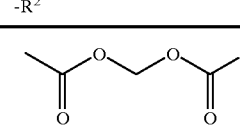 | —CH₂— | 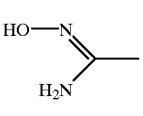 |
| 13 | 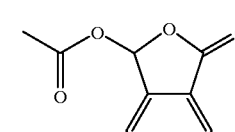 | —CH₂— | 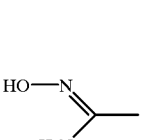 |
| 14 | 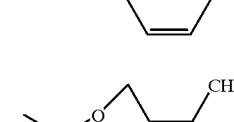 | —CH₂— | 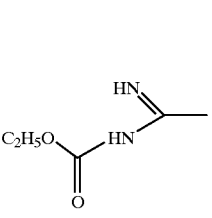 |
| 15 | 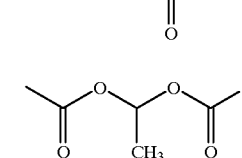 | —CH₂— | 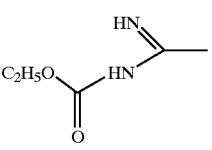 |
| 16 | 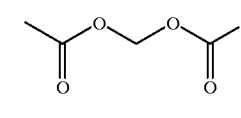 | —CH₂— | 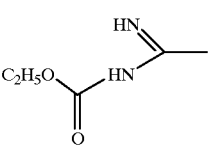 |
| 17 | 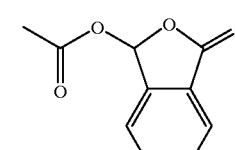 | —CH₂— | 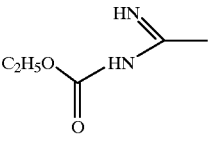 |
| 18 | 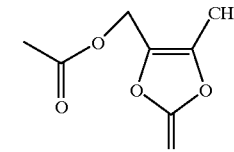 | —CH₂— | 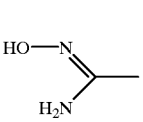 |
| 19 | 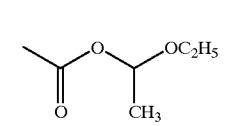 | —CH₂— | 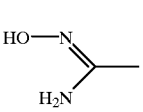 |
| 20 | 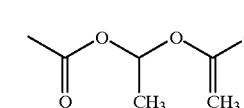 | —CH₂— | |

TABLE 6-continued
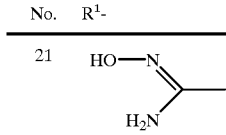
| No. | R¹- | -X¹- | -R² |
|---|---|---|---|
| 21 |  | —CH₂— | 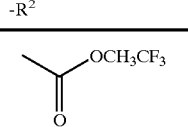 |
| 22 | 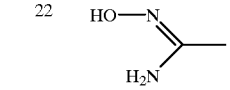 | —CH₂— |  |
TABLE 7
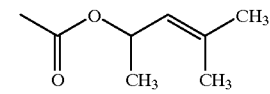
| No. | R¹- | -X¹- | -R² |
|---|---|---|---|
| 23 | 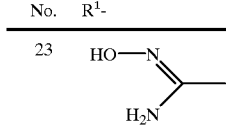 | —CH₂— |  |
| 24 | 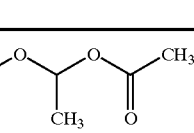 | —CH₂— | 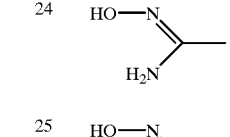 |
| 25 |  | —CH₂— | 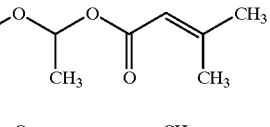 |
| 26 | 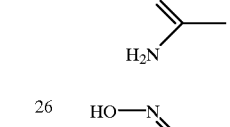 | —CH₂— |  |
| 27 | 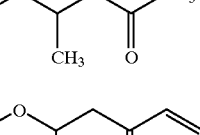 | —CH₂— | 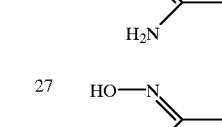 |
| 28 |  | —CH₂— | 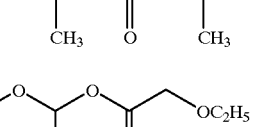 |
| 29 | 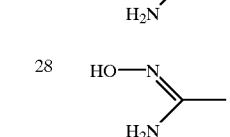 | —CH₂— |  |
| 30 | 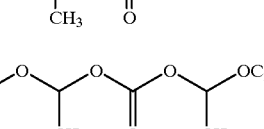 | —CH₂— | 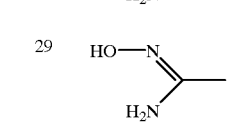 |

TABLE 7-continued
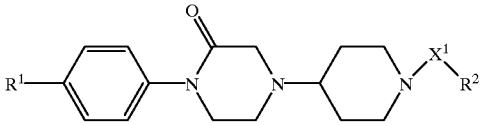
| No. | R¹- | -X¹- | -R² |
|---|---|---|---|
| 31 | 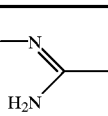 | —CH₂— | 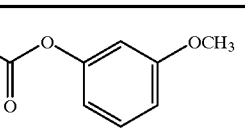 |
| 32 | 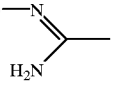 | —CH₂— | 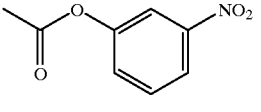 |
| 33 | 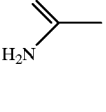 | —CH₂— | 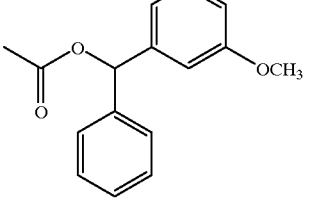 |
TABLE 8
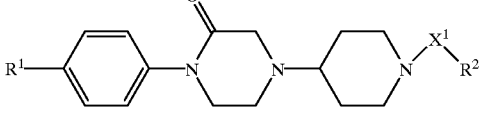
| No. | R¹- | -X¹- | -R² |
|---|---|---|---|
| 34 |  | —CH₂— | 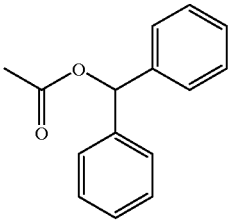 |
| 35 |  | —CH₂— | 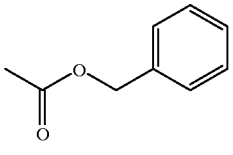 |
| 36 |  | —CH₂— | 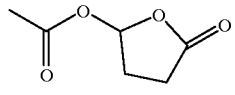 |

TABLE 8-continued
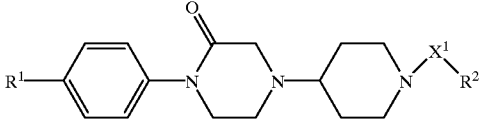
| No. | R¹- | -X¹- | -R² |
|---|---|---|---|
| 37 | 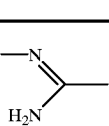 | —CH₂— |  |
| 38 | 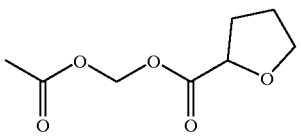 | —CH₂— | —COOC₂H₅ |
| 39 | 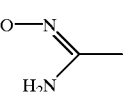 | —CH₂— | —COOCH₃ |
| 40 |  | —CH₂— | —COOH |
| 41 |  | —CH₂— | —COOC₂H₅ |
| 42 | 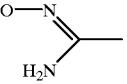 | —CH₂— | —COOCH₃ |
| 43 |  | —CH₂— | —COOH |
| 44 |  | —(CH₂)₂— | —COOC₂H₅ |
| 45 | 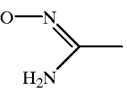 | —CH(CH₃)— | —COOC₂H₅ |

TABLE 9

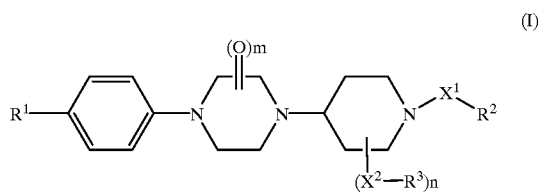

| No. | R¹- | -X¹- | -R² | -X²- | -R³ |
|---|---|---|---|---|---|
| 46 | HO—N, H₂N (amidoxime) | —CH₂— | —COOC₂H₅ | —CH₂— | —COOCH₃ |
| 47 | HO—N, H₂N | —CH₂— | —COOC₂H₅ | —(CH₂)₂— | —COOC₂H₅ |
| 48 | HO—N, H₂N | —CH₂— | —COOCH₃ | —CH₂— | —COOCH₃ |
| 49 | C₂H₅O-C(=O)-HN-C(=NH)- | —CH₂— | —COOC₂H₅ | —CH₂— | —COOC₂H₅ |
| 50 | C₂H₅O-C(=O)-HN-C(=NH)- | —CH₂— | —COOC₂H₅ | —CH₂— | —COOCH₃ |

Figure 1:
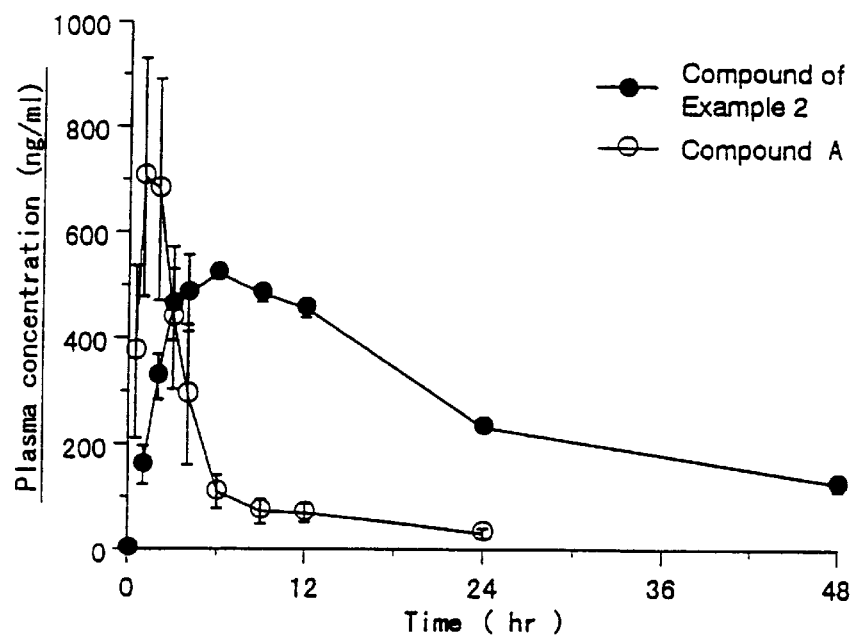
FIG. 1 represents plasma concentration-time profile of Compound A after oral administration of compound of Example 2 and Compound A to beagle dogs at a dose of 10 mg/kg (mean of three animals standard deriation)

We claim:

1. A substituted-amidinobenzene derivative of the following general formula (I) or a salt thereof:

(I)

$$R^1-\text{C}_6\text{H}_4-\text{N}\underset{(\text{O})_m}{\overset{}{\bigcirc}}\text{N}-\text{piperidine}(N-X^1-R^2)(X^2-R^3)_n$$

wherein the symbols in the above formula have the following meanings:

R¹: a group which can be converted into an amidino group in vivo;

R² and R³: the same or different and each represents a carboxyl group or a group which can be converted into a carboxyl group in vivo;

X¹ and X²: the same or different and each represents a lower alkylene group;

m: 0, 1 or 2;

n: 0 or 1, provided that n=1 when m=0.

2. The substituted-amidinobenzene derivative or a salt thereof as claimed in claim 1, wherein at least one of R² and R³ is a group which can be converted into a carboxyl group in vivo.

3. The substituted-amidinobenzene derivative or a salt thereof as claimed in claim 1, wherein the group which can be converted into an amidino group in vivo of R¹ is a group selected from the group consisting of a hydroxyamidino group, a lower alkoxycarbonylamidino group, a lower alkoxyamidino group and a lower alkanoylamidino group.

4. The substituted-amidinobenzene derivative or a salt thereof as claimed in claim 1, wherein the group which can be converted into an carboxyl group in vivo of R² and R³ is a group selected from the group consisting of a lower alkoxycarbonyl group, a lower alkoxy-lower alkoxycarbonyl group, a lower alkoxy-lower alkoxy-lower alkoxycarbonyl group, a halogeno-lower alkoxylcarbonyl group, a lower alkenyloxycarbonyl group, a lower alkanoyloxy-lower alkoxycarbonyl group, a lower alkenoyloxy-lower alkoxycarbonyl group, a lower alkanoyl-lower alkoxycarbonyl group, a lower alkenoyl-lower alkoxycarbonyl group, a lower alkoxy-lower alkanoyloxy-lower alkoxycarbonyl group, a lower alkoxycarbonyloxy-lower alkoxycarbonyl group, a lower alkoxy-lower alkoxycarbonyloxy-lower alkoxycarbonyl group, di-lower alkylamino-lower alkoxycarbonyl group, a cycloalkyloxycarbonyloxy-lower alkoxycarbonyl group, a lower alkoxybenzyloxycarbonyl group, a nitrobenzyloxycarbonyl group, a lower alkoxybenzhydryloxycarbonyl group, a benzhydryloxycarbonyl group, a benzoyloxy-lower alkoxycarbonyl group, a 2-oxotetrahydrofuran-5-yloxycarbonyl group, a 2-oxo-5- alkyl-1,3-dioxolen-4-ylmethoxycarbonyl group, a tetrahydrofuranylcarbonyloxymethoxycarbonyl group, and a 3-phthalidyloxycarbonl group.

5. The substituted-amidinobenzene derivative or a salt thereof as claimed in any one of claims 1 to 4, wherein m=1.

6. The substituted-amidinobenzene derivative or a salt thereof as claimed in claim 1, which is ethyl 4-[4-(4-hydroxylamidinophenyl)-3-oxo-1-piperazinyl]-1-piperidineacetate, methyl 4-[4-(4-hydroxylamidinophenyl)-3-oxo-1-piperazinyl]-1-piperidineacetate, ethyl 4-[4-(4-methoxycarbonylamidinophenyl)-3-oxo-1-piperazinyl]-1-piperidineacetate, methyl 4-[4-(4-methoxycarbonylamidinophenyl)-3-oxo-1-piperazinyl]-1-piperidineacetate, ethyl 4-[4-(4-ethoxycarbonylamidinophenyl)-3-oxo-1-piperazinyl]-1-piperidineacetate.

7. The substituted-amidinobenzene derivative or a salt thereof as claimed in claim 1, which is ethyl 4-[4-(4-hydroxylamidinophenyl)-3-oxo-1-piperazinyl]-1-piperidineacetate.

8. A pharmaceutical composition comprising an substituted-amidinobenzene derivative of the following general formula (I) or a salt thereof, and a pharmaceutically acceptable carrier:

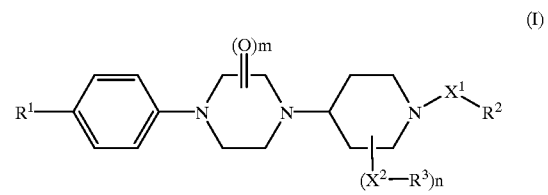

(I)

wherein the symbols in the above formula have the following meanings:

$R^1$: a group which can be converted into an amidino group in vivo;

$R^2$ and $R^3$: the same or different and each represents a carboxyl group or a group which can be converted into a carboxyl group in vivo;

$X^1$ and $X^2$: the same or different and each represents a lower alkylene group;

m: 0, 1 or 2;

n: 0 or 1, provided that n=1 when m=0.

9. The pharmaceutical composition as claimed in claim 8, which is a GPIIb/IIIa receptor antagonist.

10. The pharmaceutical composition as claimed in claim 9, which is a platelet aggregation inhibitor.

* * * * *